(12) United States Patent
Platt et al.

(10) Patent No.: US 10,614,537 B2
(45) Date of Patent: Apr. 7, 2020

(54) SYSTEMS AND METHOD FOR IMPLEMENTING BIOMEDICAL INNOVATION DATAMETRICS DASHBOARD

(71) Applicant: The MITRE Corporation, McLean, VA (US)

(72) Inventors: Leslie Platt, McLean, VA (US); Kevin Gormley, McLean, VA (US); Kenneth Hoffman, McLean, VA (US)

(73) Assignee: The MITRE Corporation, McLean, VA (US)

( * ) Notice: Subject to any disclaimer, the term of this patent is extended or adjusted under 35 U.S.C. 154(b) by 570 days.

(21) Appl. No.: 15/416,944

(22) Filed: Jan. 26, 2017

(65) Prior Publication Data
US 2017/0213307 A1    Jul. 27, 2017

Related U.S. Application Data

(60) Provisional application No. 62/287,382, filed on Jan. 26, 2016.

(51) Int. Cl.
| | |
|---|---|
| *G06F 7/60* | (2006.01) |
| *G06F 17/10* | (2006.01) |
| *G06Q 50/26* | (2012.01) |
| *G06F 19/00* | (2018.01) |
| *G06Q 40/06* | (2012.01) |
| *G16H 50/20* | (2018.01) |
| *G16H 50/50* | (2018.01) |
| *G16H 10/20* | (2018.01) |

(52) U.S. Cl.
CPC .......... *G06Q 50/26* (2013.01); *G06F 19/328* (2013.01); *G06Q 40/06* (2013.01); *G16H 10/20* (2018.01); *G16H 50/20* (2018.01); *G16H 50/50* (2018.01)

(58) Field of Classification Search
None
See application file for complete search history.

(56) References Cited

U.S. PATENT DOCUMENTS

| | | | |
|---|---|---|---|
| 2008/0215512 A1* | 9/2008 | Narzisi | G06N 3/126 706/13 |
| 2011/0093249 A1* | 4/2011 | Holmes | G06F 19/00 703/6 |

OTHER PUBLICATIONS

Over, Mead et al., "Antiretroviral Therapy and HIV Prevention in India: Modeling Costs and Consequences of Policy Options", Oct. 2006, Sexually Transmitted Diseases, vol. 33, No. 10. (Year: 2006).*

(Continued)

*Primary Examiner* — Cedric Johnson
(74) *Attorney, Agent, or Firm* — Morrison & Foerster LLP

(57) ABSTRACT

Systems and methods for implementing a biomedical innovations datametrics dashboard are presented. The dashboard can utilize data from real-world data sources to inform a simulation model which performs simulations of the biomedical innovation pipeline and related entities and processes. The dashboard can utilize the simulation model as well as feedback solicited from a user to assist in performing multi-objective optimization according to the user's preferences. The dashboard can help policy decision-makers and other stakeholders decide on a combination of policies that best incentivizes private sector biomedical innovation in order to achieve a satisfactory set of outcomes, which may include, but is not limited to, reductions in DALYs, healthcare costs, increases in industry NPV, and improved clinical trial quality.

21 Claims, 22 Drawing Sheets

(56) References Cited

OTHER PUBLICATIONS

Deodhar, Suruchi et al., "Enhancing User-Productivity and Capability Through Integration of Distinct Software in Epidemiological Systems", Jan. 28-30, 2012, IHI '12, ACM. (Year: 2012).*

Bisset, Keith R. et al., "Indemics: An interactive High-Performance Computing Framework for Data-Intensive Epidemic Modeling", Jan. 2014, ACM Transactions on Modeling and Computer Simulation, vol. 24, No. 1, Article 4, ACM. (Year: 2014).*

Bisset, Keith R. et al., "Indemics: An Interactive Data Intensive Framework for High Performance Epidemic Simulation", Jun. 2-4, 2010, ICS' 10, ACM. (Year: 2010).*

Schwartz, Ira B. et al., "Stochastic Epidemic Outbreaks: Why Epidemics Are Like Lasers", May 25, 2004, Noise in Complex Systems and Stochastic Dynamics II, Second International Symposium on Fluctuations and Noise, SPIE. (Year: 2004).*

\* cited by examiner

SYSTEMS AND METHOD FOR IMPLEMENTING BIOMEDICAL INNOVATION DATAMETRICS DASHBOARD

CROSS-REFERENCE TO RELATED APPLICATION

This applications claims the benefit of U.S. Provisional Application No. 62/287,382, filed Jan. 26, 2016, the entire contents of which are incorporated herein by reference.

FIELD OF THE DISCLOSURE

This disclosure relates to systems and methods for multiple-criteria decision-making in the domain of government incentivization of private sector investment in biomedical innovation. More specifically, the invention relates to simulation of the complex system consisting of the biomedical innovation pipeline and related entities and processes, as well as interactive methods for multi-objective optimization to support a satisficing decision process using the results of the simulation. These systems and methods can be used to improve the performance of public and private sector interactions in the field of biomedical innovation.

BACKGROUND OF THE DISCLOSURE

This disclosure relates to systems and methods for multiple-criteria decision-making in the domain of government incentivization of private sector investment in biomedical innovation. More specifically, the invention relates to simulation of the complex system consisting of the biomedical innovation pipeline and related entities and processes, as well as interactive methods for multi-objective optimization to support a satisficing decision process using the results of the simulation. These systems and methods can be used to integrate pertinent information sources to simulate public and private sector interactions and to facilitate decision-making that satisfices multiple competing objectives in the field of biomedical innovation.

Organizations engage in research and development (R&D) in an attempt to spur innovation in the various fields in which they are engaged, while at the same time maximizing value to the organization.

Currently, much of R&D planning involves private institutions and private sector organizations maximizing the expected net present value (NPV) (i.e., the net sum of funds being expended and received) and other financial metrics of their R&D portfolio through selecting and scheduling projects. Private sector organizations can also consider time, money, risk, resource constraints and project interactions (e.g. dependencies on the success of precedent projects) when determining which research projects to pursue. In the field of public health, the planning of R&D projects may need to take into account other factors that may not be present in other fields. For instance, public health research and development projects may need to take into account public health influences such as Disability Adjusted Life Years (DALY) burden relief, and public health spending reductions that may be implemented by the government. However, often times these factors are given little weight or are not considered at all.

Governmental organizations, through the implementation of policy, distribution of funds, and other incentivizing activities, can often impact private sector research. For example, U.S. Department of Health and Human Services (HHS) policy decisions (funding of basic and applied research, regulation of new biomedical innovations (e.g. parallel review for breakthrough drugs), payment policies for new biomedical innovations, etc.) may encourage private sector research in specific biomedical areas and conditions, including but not limited to biomedical innovations such as drugs, biologics, vaccines, diagnostics, and devices. However, the government organization trying to impact research and development may not be able to anticipate the overall response of the private R&D industry to those policies, or the potential impact on DALY burden relief and public health spending reductions. The impacts of current or planned policies by other government agencies such as tax incentives and by non-governmental organizations such as disease foundation sponsored research are also rarely considered in an integrated manner.

Multiple-criteria decision-making can be essential to the effective operation of many organizations. Decision-makers often implicitly, if not explicitly, attempt to simultaneously balance multiple competing requirements and goals. This is made more challenging when the outcomes of decisions are not obvious or easily predictable.

The biomedical innovation ecosystem—that is, the entities compromising, influencing, and influenced by the biomedical innovation pipeline, and the relationships between them—can be considered a complex adaptive system, characterized by complex and nonlinear interactions and interdependencies. Government policies can shift with new administrations or changes in budget, and policies of different government agencies can have an effect on one another, e.g. National Institutes of Health (NIH) research funding and the U.S. Food and Drug Administration (FDA) approval process may influence drug development, which will in turn affect disease prevalence and health outcomes, which are relevant to HHS, as well as Centers for Medicare & Medicaid Services (CMS) healthcare costs. The response of pharmaceutical companies and private sector organizations to changes in government funding and incentives is difficult to predict, and the magnitude of their response may not be proportional to the magnitude of policy change.

Multiple-criteria decision-making with regard to the biomedical innovation ecosystem can pose many challenges. One challenge is the complexity of the domain. For instance, risk and uncertainty can make it difficult to predict private sector response to new policies, the outcome of research or clinical trials for new biomedical innovations, how widely the innovations will be adopted if successful, the future presence of competing technologies, or the resulting health outcomes. Complex interactions between entities, interdependencies in their behavior, and nonlinear relationships between input parameters and outcomes further exacerbate these problems.

Another challenge faced in multiple-criteria decision-making with regard to the biomedical innovation ecosystem is computational intractability. In particular, the decision space of potential sets of policy decisions and budget allocations is too large to permit an exhaustive search of all possibilities. Therefore, algorithms are needed to cleverly traverse the space in search of policy options with desirable outcomes.

Even with the use of an efficient optimization algorithm, a further challenge of multiple-criteria decision-making with regard to the biomedical innovation ecosystem lies in the need for subjectivity in balancing competing objectives. In multi-objective optimization, there is often no single solution which is optimal with respect to all objectives, thus requiring subjective trade-off decisions. Such decisions may be intuitive for a human decision-maker, but may be difficult to translate into mathematical language that an automated algorithm can utilize.

Thus, a system that can simulate the biomedical innovation ecosystem and perform multi-objective optimization in support of multiple-criteria decision-making can prove to be valuable.

SUMMARY OF THE DISCLOSURE

Accordingly, systems and methods for satisficing government policy decisions that achieve a relatively high utility for a variety of factors are provided. The variety of factors can include: 1) reducing the Disability Adjusted Life Year (DALY) burden, 2) reducing public health costs [particularly, Health and Human Services (HHS) costs], 3) increasing biomedical industry net present value (NPV), and 4) quality standards present in the biomedical field. A microsimulation that utilizes nested stochastic optimization and perturbation algorithms that encompass public and private sector interactions can be used by governmental agencies to simulate, formulate, and evaluate government policy decisions and give those agencies a reasonable representation (through a nested optimization) of how private sector R&D investments would likely respond to various governmental initiatives. The simulation model can be continuously updated with new data so as to update government policy decisions, private sector responses, and the resulting impacts.

In one embodiment, a computing system can include four modules: a data module, a simulation module, an optimization module, and an executive module that can work in conjunction with one another to import data from external sources and use that data to generate satisficing solutions to various desired outcomes relating to biomedical innovation.

The data module can import data from real-world data sources—including, but not limited to, clinical trial data, demographic data, and budgetary constraints—and can use the data to infer model parameters.

The simulation module can perform simulations of the biomedical innovation ecosystem using parameters inferred from the data module, constraints and objectives specified via the executive module, and policy decisions specified by the optimization module or the executive module. This may entail, but is not limited to, defining models of the following: policy options, budget allocations, private sector response to policy changes, the biomedical innovation pipeline, the healthcare delivery system, disease prevalence, and population dynamics.

The optimization module can include an interactive multi-objective optimization algorithm, which solicits feedback from human decision-makers via the executive module and utilizes predictions from the simulation module in order to identify a set of policy decisions that best achieves multiple competing objectives and desired outcomes while satisfying the specified constraints.

The executive module can include an interface through which human decision-makers can specify constraints and objectives to the simulation module, provide feedback to the optimization module, and view visualizations to compare and illustrate the predicted impact and outcomes of policy decisions.

BRIEF DESCRIPTION OF THE DRAWINGS

Figure 16B:
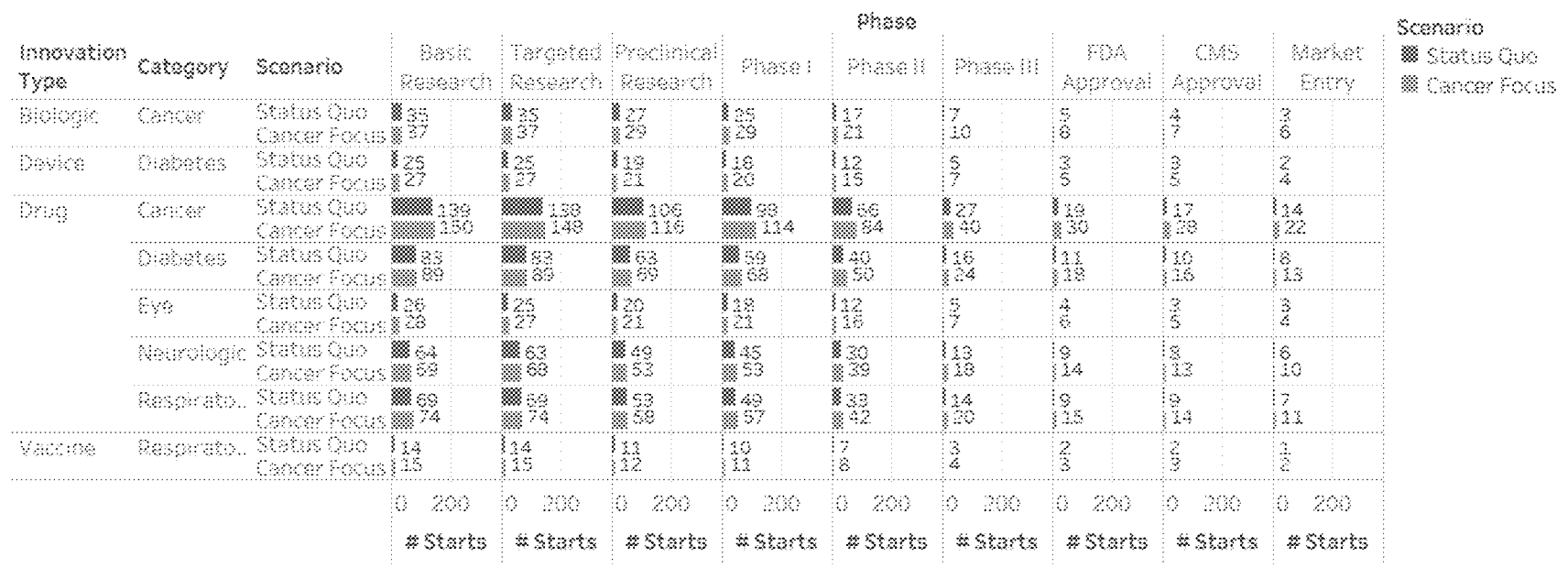
Figure 16C:
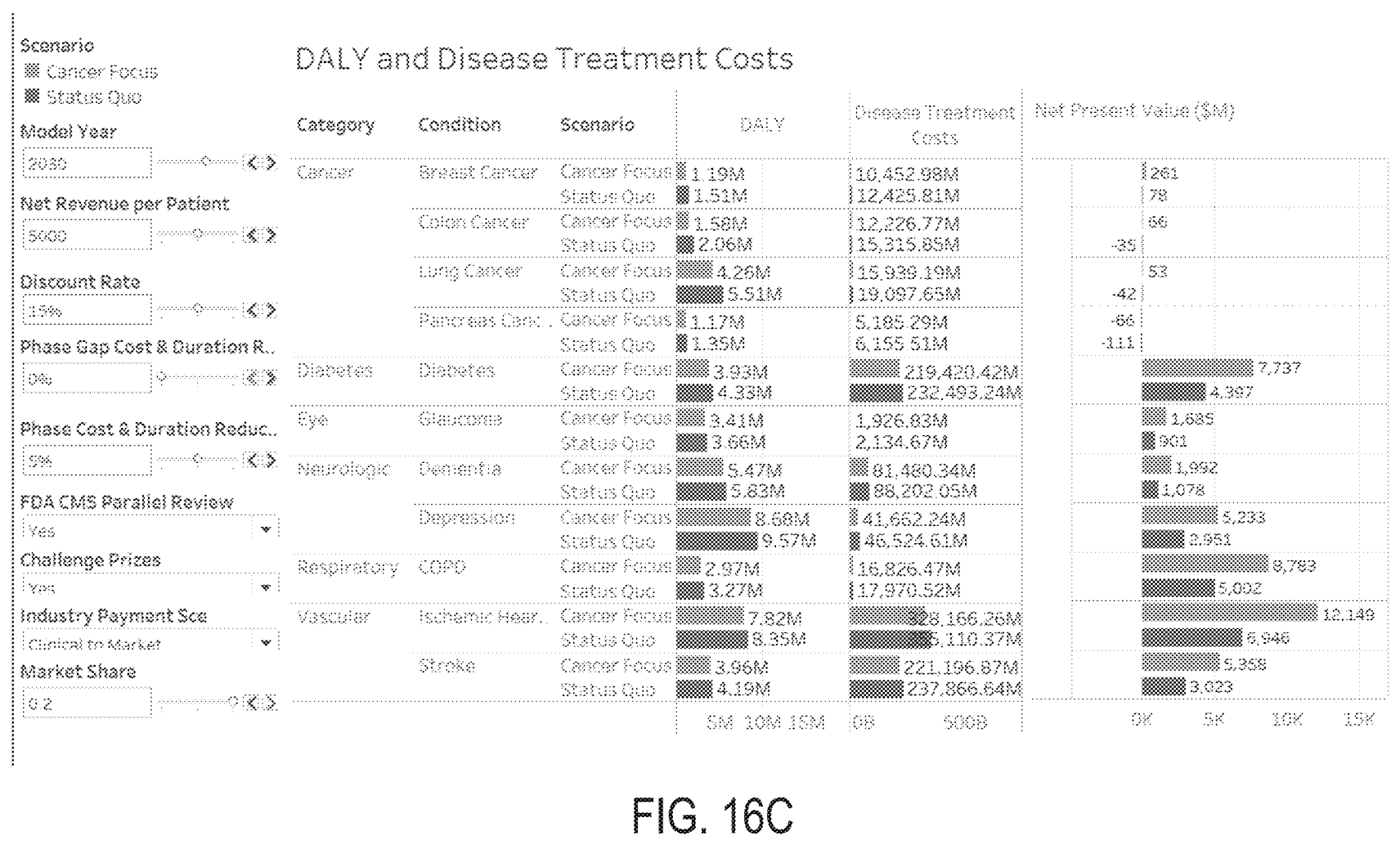

FIGS. 16a-e illustrate various exemplary dashboards displayed to a user according to examples of the disclosure.

DETAILED DESCRIPTION

Figure 1:
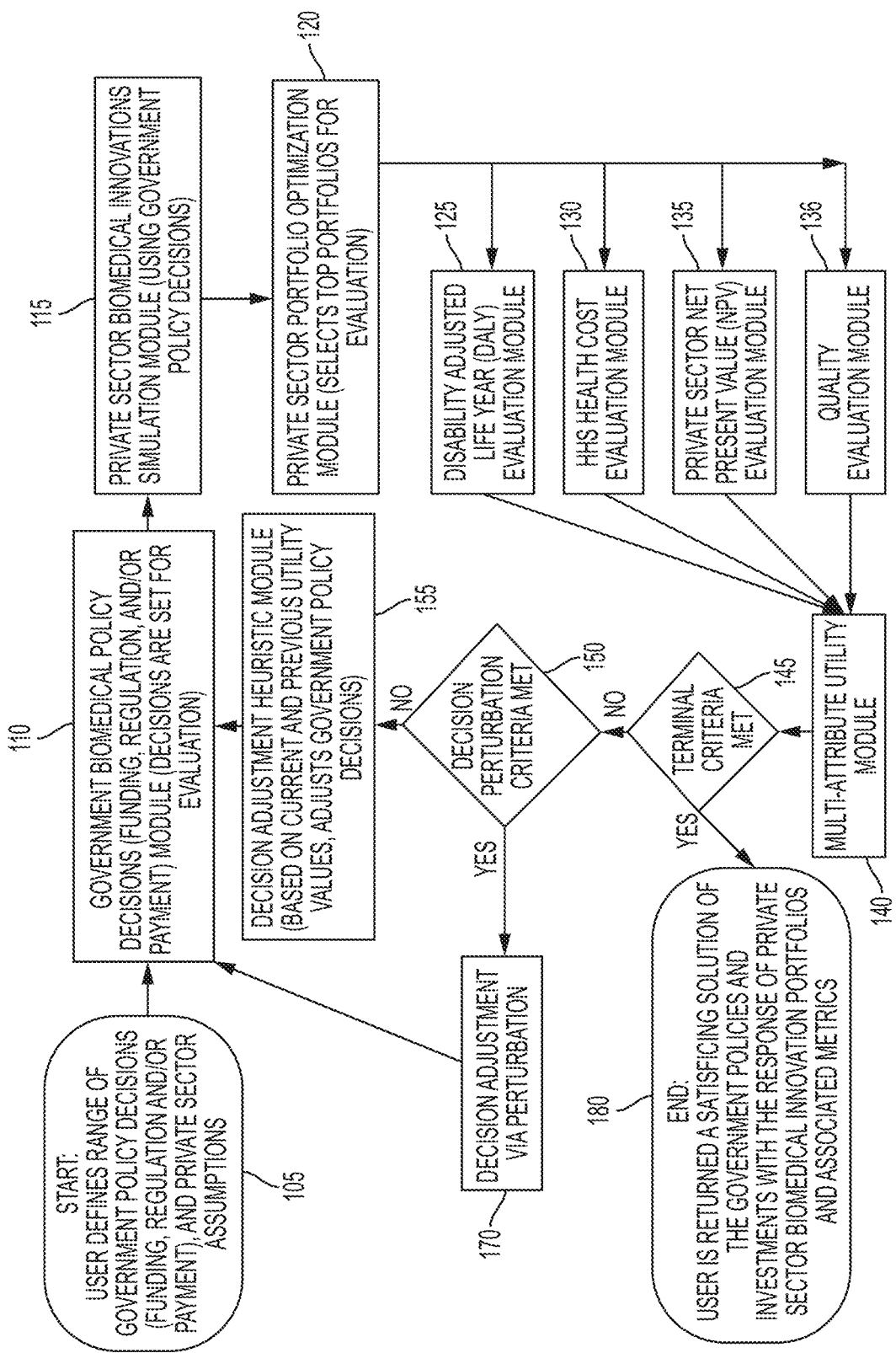
FIG. 1 illustrates an exemplary method that utilizes microsimulation to determine satisficing solutions using a nested optimization problem and perturbation process as a search mechanism according to examples of the disclosure.

Described herein are systems and methods for implementing a biomedical innovation datametrics dashboard (BIDD) system. The systems and methods described herein can be used to provide governmental agencies or other private sector organizations the ability to simulate the effect of policy initiatives on private research and development efforts that exist within the private sector.

The systems and methods employ analytical tools designed to simulate, formulate, and evaluate governmental policy decisions and their effect on private sector R&D investments. The simulation model can be continuously updated with new data so as to update government policy decision, private sector responses, and the resulting impacts.

The systems and method presented herein can enable government decision makers to identify satisficing solutions of promising government policy decisions (including, but not limited to, funding, regulation, and payment) that will reduce expected DALY burden and HHS costs. Satisficing can mean finding a reasonably good solution that satisfies a set of conditions or constraints and stakeholder objectives, rather than finding a unique optimal solution, which may not exist or be attainable given the complexity of the model, computational limitations, and presence of competing objectives.

For each set of government policy and investment decisions, there can be a nested stochastic optimization problem that is solved for what the private R&D industry does at a macro level. The purpose of the simulation is not to predict what specific drugs/devices/biologics/etc. a particular private sector organization or research institute will pursue, but rather what innovations are most likely to be part of the overall, industry-wide private sector portfolio and the associated levels of investment. Evaluating multiple likely portfolios (based on NPV estimates of innovation, a model of competition, and a model for the size and flexibility of innovation type and condition sectors [e.g., breast cancer drugs]) and simulating many trials of outcomes (what innovations are successfully completed to enter the market) can result in a probabilistic range of impacts for such metric as DALY burden, costs to the governmental organization and industry NPV.

Initially, each biomedical innovation can be evaluated one at a time for its NPV in isolation (assuming no competition). Based on its initial NPV estimate, each innovation's probability of being selected can be estimated. Based on the probabilistic number and timing of competitive innovations, the NPV of each innovation can be adjusted. In one example, if two breast cancer drugs with high NPV are estimated to come to market at the same time, this will decrease each one's market share and lead to lower estimates of NPV.

The user of the simulation in the government role can maximize a utility function of DALY burden relief and government cost savings (and private sector NPV) by deciding how to change the constraints that the private sector organizations face in the traditional R&D planning model.

The unique features of the micro-simulation satisficing method address specific analytic weaknesses of existing satisficing methods; principally the dependence of solutions on the starting point and path for searching the solution space and the lack of pertinent criteria for stopping the search. The nested optimization process coupled with perturbation analysis provides an improved basis of identifying more promising solution regions and stopping points for discrete parameters in non-linear space.

In summary, the method is the means of performing the function of integrating disparate data sources to simulate the complex private investment patterns as influenced by public policies and processes.

FIG. 1 illustrates an exemplary method that utilizes microsimulation to determine satisficing solutions using a nested optimization problem and perturbation process as a search mechanism according to examples of the disclosure.

The method can begin at step 105, wherein the user defines the range of potential government policy decisions (funding, regulation and payment). Assumptions on the private sector model can also be made. In addition, the user can select certain model parameters such as the number of private sector portfolios to model, the number of simulations per portfolio, how to weight the utility functions, and how many total cycles to run.

Once the user defines the ranges of governmental policy decisions, the method can move to step 110 wherein the simulation model is run for a first-time. At step 110, the decision variables can be initialized to what the user specified at step 105, or a random initial solution based on a random seed. The variables that outline the governmental biomedical policy decisions (i.e., funding, regulation, and payment) can be set using a three stage process. In stage 1 of this method, the decision variables of the phase gaps (i.e., time periods between phases of a research project such as basic research, proof of concept, pre-clinical research and develop, and human trials) are explored, while the other variables are set to central values. In stage 2, the best phase gap values from stage 1 are locked, and the parallel review variables are explored. In stage 3, the best phase gap values from stage 1 and the parallel review variables from stage 2 are locked, and the innovation investment variables are explored. In stage 4, the values from the previous 3 stages are set and then perturbed to find potentially better solutions.

Once the variables are set in step 110, the method can move to step 115 wherein individual private sector innovations are simulated for their success and failure and potential NPV.

After the individual innovation NPVs are calculated in step 115, the method can move to step 120 wherein a sequential set of NPVs is calculated that can consider the value of an innovation given that other competitive innovations may be available. After a set of iterative recalculations of NPV given the portfolio, the NPVs can converge within a given pre-defined tolerance. A set of simulations can create portfolios based on each innovation's probability of being funded. For expected NPV at or below 0, the probability of funding is near 0, as NPV increases, the probability of funding slowly increases, then rapidly increases, then levels off approaching probability one for very high NPV values. Thus, this S-shaped curve defines the relationship between NPV and funding probability. A "knapsack" problem formulation can calculate the best set of innovations given the NPV for the relative price and the available budget for that category. Category constraints (so many devices, drugs, biologics; and so many in each condition) can be estimated as inputs.

Upon the completion of step 120 the simulation can be conducted using a series of utility functions that can assess the innovations based on various factors. Utility function 125 can be applied wherein DALY burden is calculated based on a very rough estimate of how much an innovation may relieve the DALY burden. (Diminishing marginal returns apply for multiple innovations that serve the same condition).

Another example of a utility function is illustrated at 130 wherein the governmental organization cost module can be applied. The governmental organization utility function 130 can have rough order of magnitude costs for the modeled conditions and the approximate number of patients in that condition. A simple model can estimate the percent reduction in future expected costs. (A single value, rather than cash flows in a particular year. The short term cure may be more expensive than maintenance in the short term, but cheaper of a patient's lifetime.)

In utility function 135, the private sector NPV is calculated based on the modeled portfolios and trials. A risk-adjusted NPV can be modified to penalize extreme scenarios (lots of risky, failed projects) by assigning them lower utility values.

In utility function 136, the quality aspect of the innovation as a subject of considerable nuance can be assessed. This refers specifically to the adherence to a defined set of appropriate and sufficient standards and practices of the scientific activity (research, preclinical or clinical development, etc.) that ensures that the work proceeds in an appropriate manner. In such a manner, all non-scientific risks (e.g., execution risk) are drastically reduced, and innovation is able to proceed with improved confidence. Such standards should be composed of only those elements which are needed to meet this goal, and should be minimally burdensome to the innovators while simultaneously protecting the interests of the innovation funders and financiers. The use of such standards in clinical trials is of paramount importance given the resource-intensive nature of this activity, and there is no shortage of organizations with considerable interest and expertise in ensuring accountability in Health, Health Care and Biomedical Research (e.g., ACRES and The Healthcare Quality Foundation).

At present, there are a multitude of policy option combinations available, and this reflects an intrinsic problem with the system. While the multitude of options available can be burdensome to a user, nonetheless, it also offers the opportunity to find the most appropriate solution without starting de novo. The simulation can offer guidance as to the development and form that would meet these criteria. For example, regarding validity, international standards (e.g., ISO 14155, which covers GCP for clinical trials medical devices) are more likely to be accepted, and acceptable to a wider array of innovation participants, than country-specific ones, even those originating in the US. Regarding form, the U.S. Food and Drug Administration Guideline for Industry (ICH E3, 1996) for the Structure and Content of Clinical Study Reports is in a much less desirable format than the Consort Transparent Reporting of Trials checklist of 2010. STROBE and STREGA, which build on CONSORT, are good first efforts in using such checklist-style approaches to observational (epidemiological) and genetic association research.

At step 140, a multi-attribute utility model can weigh the 4 utility functions (125, 130, 135, and 136) to consider the DALY burden, HHS costs, private sector NPV, and quality. Step 140 can be divided into 4 stages. In stage 1 of step 140, the weight is (primarily or even exclusively) on DALY burden 125, in stage 2, the weight is (primarily or even exclusively) on HHS costs (utility function 130), and in stage 3, the weight is (primarily or even exclusively) on industry NPV (utility function 135). In stage 4, all utility function components are considered and given weight according to user preferences set at the beginning of the simulation.

At step 145, if the terminal criteria are met (a certain number of trials, no improvement after a predetermined number of trials and a predetermined number of perturbations), then the simulation can move to step 180 wherein the simulation is terminated. Satisficing criteria such as a specified percentage decrease in expected DALY burden, a percentage decrease in expected governmental organization costs, and/or a specified percentage increase in industry NPV can be applied. In one example, after a maximum number of trials, the simulation will stop with the best available solution even if it is below the satisficing criteria. The parameter for maximum trials could be increased and/or the satisficing criteria could be relaxed [made easier to obtain]. At step 180, upon termination, the simulation can produce a satisficing solution with detailed outputs and metrics.

However, if the terminal criteria are not met at step 145, the simulation can move to step 150 wherein perturbations can be introduced to "break" the current set of decision variables free from its current decision space. At step 150, if the decision perturbation criteria are met, then the process can move to step 170 wherein a set of perturbations (random adjustments to the decision variables) are added to step 110 and the simulation is run again.

If, however, the decision perturbation criteria are not met, then the process can move to step 155. At step 155, if the terminal criteria and perturbation criteria are not met, then a heuristic can be applied to improve the decision variables. In stage 1 of step 155, the gap durations (i.e., time between phases of a research project) can be decreased by a proportion of the range until NPV decreases and then the gap durations are increased. In stage 2 of step 155, the parallel review decisions can be adjusted to improve the condition which had the least improvement in the DALY burden. In stage 3 of step 155, the governmental organization cost relief of the conditions that are the smallest receive additional investment.

In stage 4 of step 155, a genetic algorithm method can evaluate a variety of nearby decision solutions with a chance of a farther away decision solution. Solutions with the highest utility reproduce similar decisions in the subsequent generations.

Figure 2:
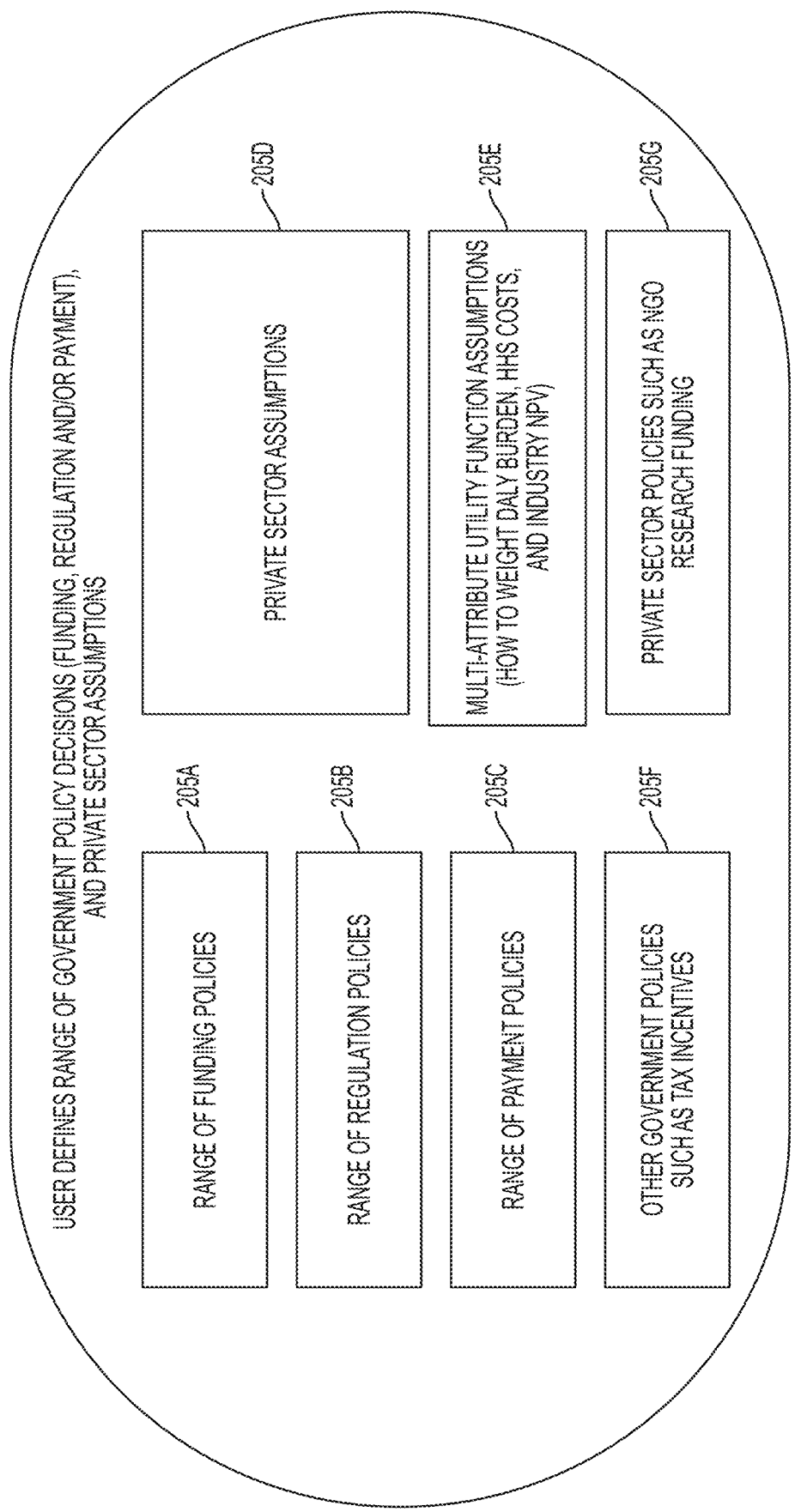
FIG. 2 illustrates an exemplary variable selection space according to examples of disclosure.

FIG. 2 illustrates an exemplary variable selection space according to examples of disclosure. The variable space illustrated in FIG. 2 can represent the variables that a user can set in step 105 of FIG. 1. Variable 205A can represent the range of funding policies such as the budget allocation for innovation types and conditions (e.g., drugs related to breast cancer).

Variable 205B can represent the range of regulation policies such as the number of expedited, parallel reviews for high priority conditions. Regulation policies can also include a policy of having explicitly defined targets and taking into account the research quality based on established criteria, for meeting those targets.

The simulation model of FIG. 1 can demonstrate the potential impact of the quality of 1) having the right research techniques and protocols being performed, and 2) executing the research effectively, on the risk of failure during the FDA approval process. In one example, a simple model is used initially with larger error bounds on low quality research and smaller error bounds on high quality research that show the probability of meeting a target is more likely with higher quality research. When available, actual data can be fed into the model to provide a more accurate representation.

Variable 205C can represent the range of payment policies such as guaranteed payment for reaching milestones for treatment in certain conditions.

Variable 205D can represent private sector assumptions such as the size of industry in the innovation type and condition sectors and the current pipeline of innovations.

Variable 205E can represent user preferences for how to weight the three utility function components of DALY burden, governmental organizational costs and industry NPV.

Variable 205F can represent other government policies such as tax incentives to encourage research and development (in certain conditions or overall) can be modeled.

Variable 205G can represent private sector policies such as research funding by non-governmental organizations (such as disease advocacy foundations) can be included in the model.

Figure 3:
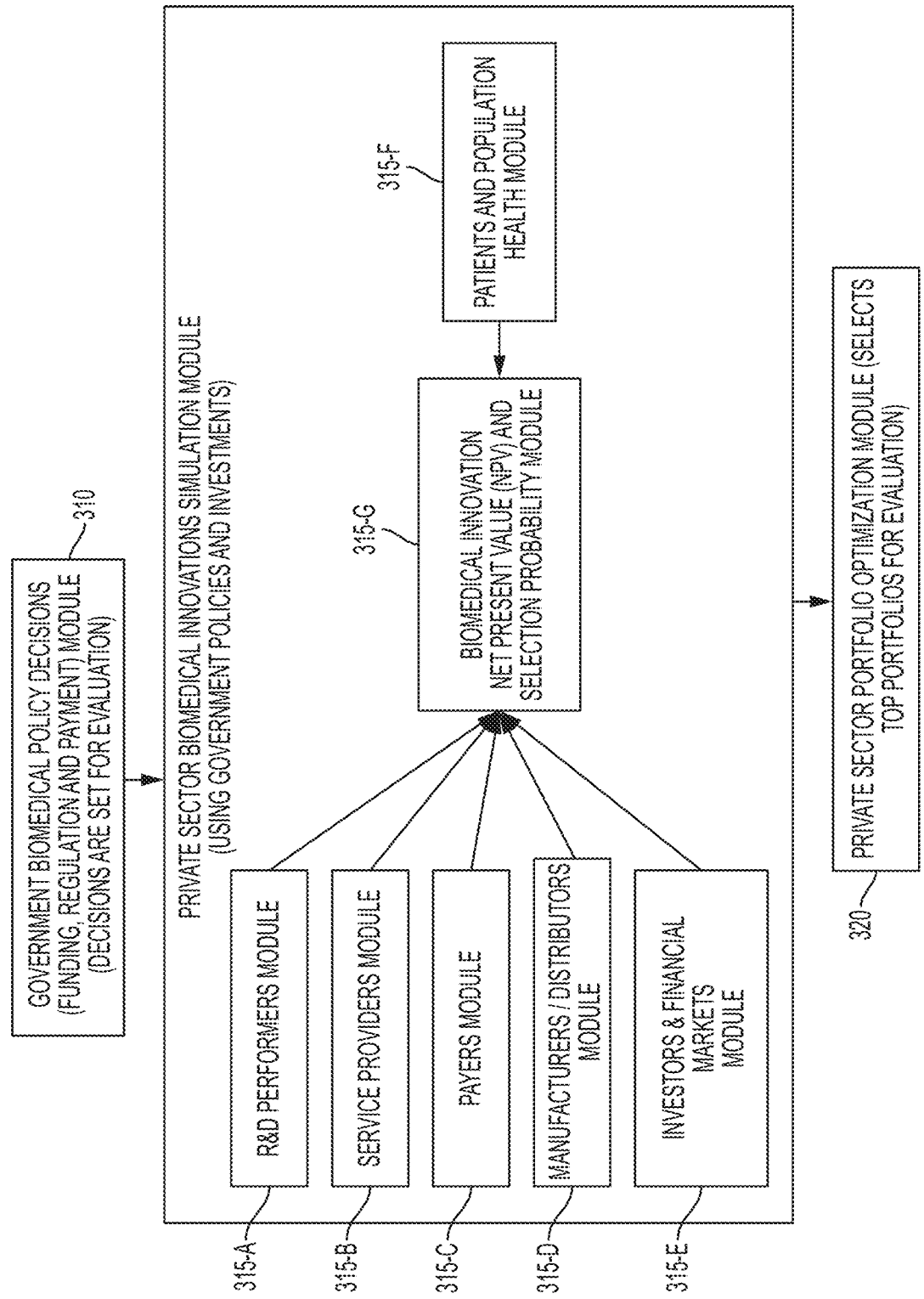
FIG. 3 illustrates an exemplary private sector NPV module according to examples of the disclosure.

FIG. 3 illustrates an exemplary private sector NPV module according to examples of the disclosure. The exemplary private sector NPV module illustrated in FIG. 3 can represent a detailed model of step 115 illustrated in FIG. 1.

As discussed with respect to FIG. 1, the private sector biomedical innovations module 115 can respond to the government policies set by a user of the simulation model at step 105.

Stakeholders 315A, 315B, 315C, 315D and 315E can represent entities that have a certain capacity and cost structure to "supply" the research and development. Government policies are still applied.

Module 315F can represent a module of the "demand" that defines how many patients have each medical condition over time and what comorbidities they have. This pool of patients represents the potential market for a given innovation that treats patients for one or more conditions.

Module 315G can calculate the NPV and selection probability for each innovation based on the supply and demand.

Figure 4:
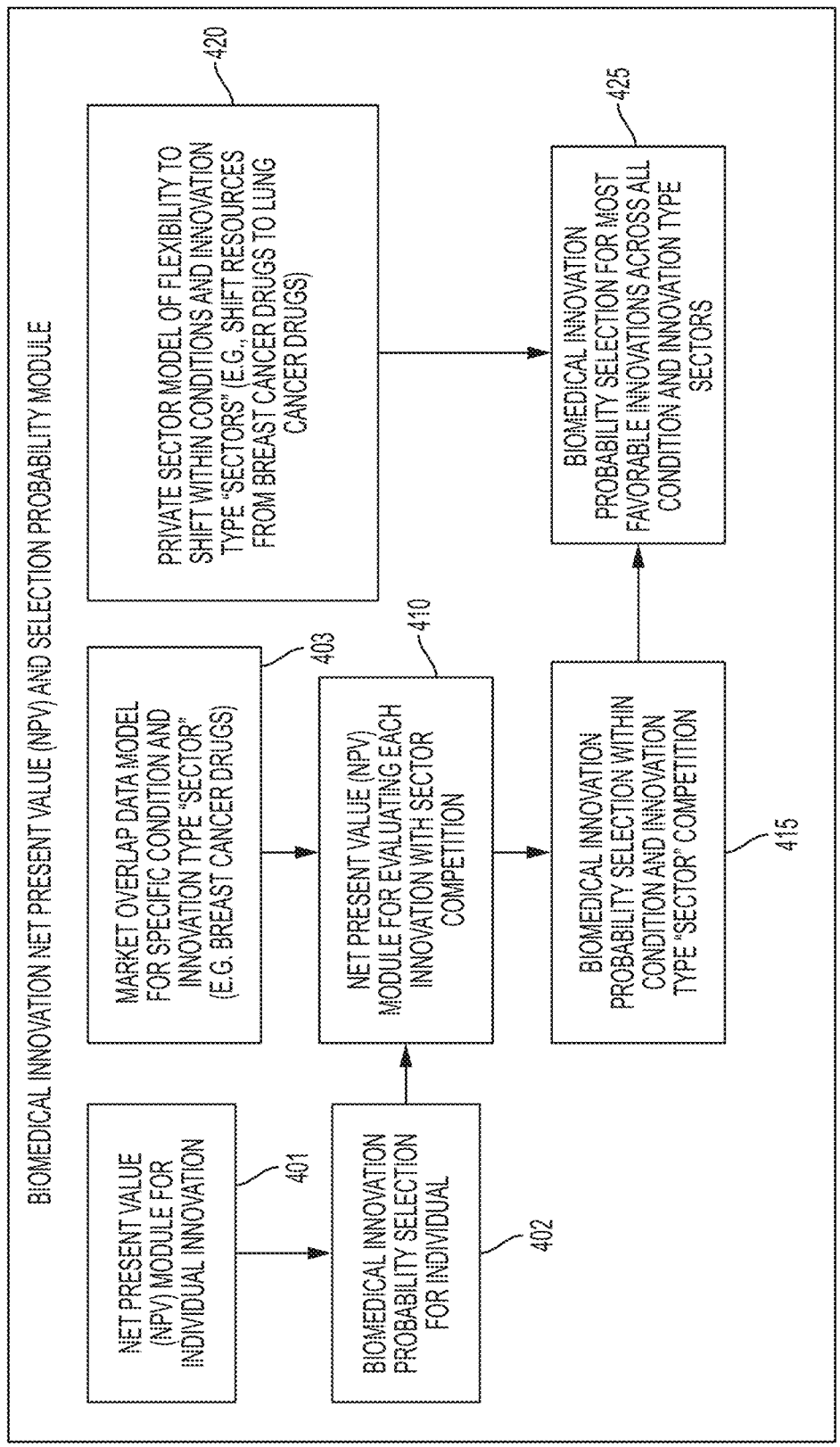
FIG. 4 illustrates exemplary biomedical innovation NPV and selection probability module according to examples of the disclosure.

FIG. 4 illustrates exemplary biomedical innovation NPV and selection probability module according to examples of the disclosure.

Module 401 can calculate the basic NPV for an innovation in isolation. Module 402 can calculate the probability for selection based on the basic NPV for each innovation in isolation. Module 403 can include a data table of the estimated overlap there is among innovations to treat the same condition. Module 410 can calculate the NPV given the overlap among innovations and the initial probability of them being selected.

Module 415, based on the adjusted NPV given market competition in 410, can provide a new estimate for the probability of being selected.

Module 420 can include a data table that includes data indicating how much flexibility the industry has to expand or contract in certain innovation type and condition combinations (e.g., shifting resources).

Module 425 can calculate an overall probability of being funded for each innovation given the industry's flexibility to expand or contract in certain innovation type and condition combinations.

Use Cases for the Simulation

Governmental organizations can use the simulation presented above for generating initial sets of decisions to guide strategic discussions, to evaluating individual policies, and to communicate with the biomedical private sector more effectively. In one example the governmental organization can use the satisficing solution to generate promising starting solutions that reduce DALY burden, HHS costs and increase NPV, to guide HHS strategies.

Additionally, the governmental organization can use the simulation model to evaluate funding policies to understand the impacts for shifting funding priorities to high priority conditions and use such information to make the public case for a higher research budget to demonstrate the overall HHS cost savings by bringing more biomedical innovations to market sooner. The governmental organization can further evaluate regulatory policies to understand the impacts and evaluate payment policies such as milestone payments and challenge prizes to be an innovation buyer.

The simulation presented above can supplement a private sector biomedical corporation's proprietary decision models. As an example, a private sector biomedical corporation can add their portfolio to the private sector pipeline and evaluate additional research projects under consideration. The simulation can also be used by a private sector biomedical corporation to evaluate the impact of proposed government policies and incentives to see how their research portfolio could respond to take advantage of incentives. The simulation can provide a private sector biomedical corporation with a clearer view of competitive and cooperative research, thus adding more transparency which may help private sector organizations make better decisions. (Rather than let a promising drug target languish because a new drug is expected to enter the market, a company may sell it.)

The simulation can be used by research institute, which can add their portfolio to the private sector pipeline and evaluate additional research projects under consideration. Additionally, a research institute can use the simulation to evaluate the impact of proposed government policies and incentives to see how their research portfolio could respond to take advantage of incentives such as milestone payments.

The simulation described above can be used by institutional investors to supplement proprietary models by showing how portfolios of R&D investments take advantage of government policies. Institutional investors can utilize the simulation tool to generate candidate portfolios of biomedical innovation megafunds (large funds of biomedical innovations that diversify risk) that treat a given condition and have a specified expected reduction in DALY burden and evaluate the impacts if investors expand the overall biomedical innovation industry and bring more innovations to market earlier.

Given how the private sector funds R&D where an investment should have positive return over its lifecycle (NPV>>0) and the government's resource constraints, select incentives (innovation grants) and policies (reduced gaps and parallel review) to maximize a [multi-attribute utility] function of DALY burden relief and HHS cost savings (and possibly private sector NPV) a satisficing solution can be represented mathematically. Alternatively, the utility functions employed in the simulation, can be a satisficing function that rewards meeting criteria of achieving a specified reduction in DALY burden, reduction in HHS costs and increase in industry NPV.

Let the biomedical innovation satisficing problem be defined as follows:

Let biomedical innovation be b=1 to B
Let phase be p=1 to P
Let condition be c=1 to C
Let innovation category be g=1 to G
Let time period be t=1 to T (as an example, t can be expressed in months)

An innovation applicability matrix A can be used to show what biomedical innovation b applies to what condition c. An element of matrix A can be expressed as:

$$A_{bc} = \begin{cases} 1 & \text{if innovation } b \text{ treats condition } c \\ 0 & \text{otherwise} \end{cases}$$

For an innovation category g (such as drugs, devices, biologics or diagnostics), and condition c (such as breast cancer, lung cancer, or diabetes), there is an industry matrix defining the size in dollars.

Dollars can be used as a proxy for the overall capacity to do research or development. As an example, if private industry has been doing $1 billion of applied research in diabetes, there may be capacity to increase a certain amount in the following year, but there is a limit.

Let V be defined as capturing the decision if the private sector conducts research of biomedical innovation b for phase p in period t, and S be the success of that research:

$$V_{bpt} = \begin{cases} 1 & \text{if innovation } b, \text{ phase } p \text{ is funded in period } t \\ 0 & \text{otherwise} \end{cases}$$

$$S_{bpt} = \begin{cases} 1 & \text{if innnovation } b, \text{ phase } p \text{ successful in period } t \text{ [or previously successful]} \\ 0 & \text{if innovation } b, \text{ phase } p \text{ success is still uncertain} \\ -1 & \text{if innovation } b, \text{ phase } p \text{ is unsuccesful (or unable to be successful)} \end{cases}$$

$$S_{bt} =$$

$$\begin{cases} 1 & \text{if innovation } b \text{ is successful across all phases in period } t \\ 0 & \text{otherwise} \end{cases}$$

Let DALY burden relief of condition c by biomedical innovation b be $D_{cb}$, where 0.1 is 10% relief, 0 is 0% relief, 1 is 100% relief; [0.01-0.10 may be typical].

Let the reached population with condition c by biomedical innovation b be $R_{cb}$ Let the national DALY burden for condition c in time period t be $N_{ct}$ For the purposes of example, let current DALY burden for condition c be $N_{c, 2015}$ Population growth and changing demographics (again population) can influence growth over time.

Infectious diseases may spread according to epidemiological models (prevalence, infection rate, treatment rate, cure rate, death rate, etc.).

If there was only one innovation that was available ($S_{bt}=1$), the DALY Burden Savings would be:

$$N_{ct} * D_{cb} * R_{cb}$$

Let $O_{cij}$ be the reduction overlap for condition c for innovation i∈B and j∈B, If innovation i and j are both in effect (available) in time period t, then the DALY Burden Savings over all innovations would be:

$$N_{ct} * \text{product over all i and j}[1-(D_{ci}*R_{ci}*O_{cij})]S_{it}*S_{jt}$$

Let M capture the HHS Savings on condition c by innovation b:

$M_{bc}$=fraction of money saved by having condition c treated by innovation b

Let X, Y and Z capture government policy decisions:

$X_p$ = gap length for phase $p$ $Y_b = \begin{cases} 1 & \text{parallel review by } FDA \text{ and } CMS \text{ for innovation } b \\ 0 & \text{otherwise} \end{cases}$ $Z_c$ = government investment in millions of dollars for condition $c$ (allocated to fund additional innovations for that condition)

Example Satisficing Equation:

Maximize $E[\text{sum over } t=1 \text{ to } T \text{ of } (k1\ U1(\text{DALY Burden Savings})/(1+R1)^t + k2\ U2(\text{HHS Savings})/(1+R2)^t + k3\ U3(\text{Private Sector NPV})/(1+R3)^t]$ U1, U2 and U3 can be utility functions based on the likely private sector biomedical innovation portfolios that are influenced by the government policies and investments.

k1, k2, and k3 can be coefficients to weight the three utility functions.

R1, R2 and R3 can be discount rates to make the future utility or value less valuable than current utility or value.

Subject to constraints:

Probability of funding an innovation given the anticipated NPV $V_{bpt}=0$ if $NPV_b<0$ (investments will only be made for profitable innovations)

Figure 5:
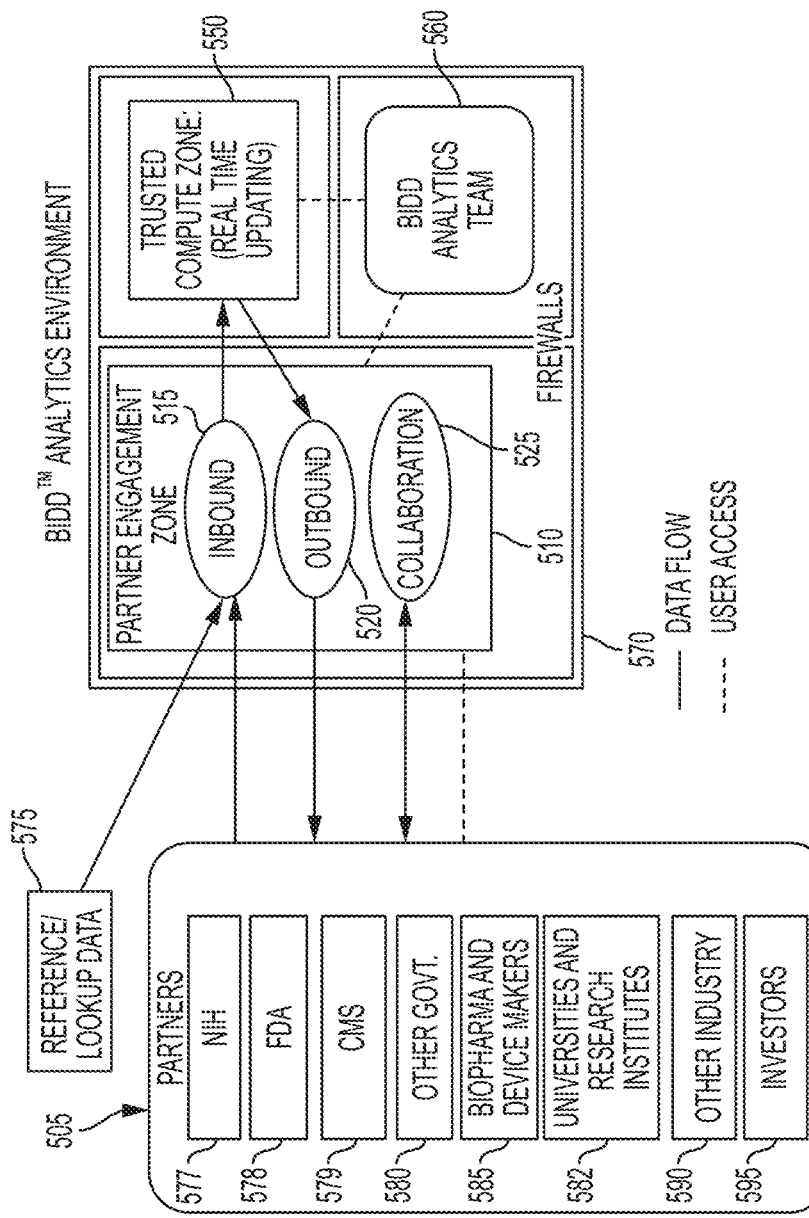
FIG. 5 illustrates an exemplary computer system upon which examples of the disclosure can be implemented.

$V_{bpt}=0$ if $S_{b,p-1,t-1} \neq 1$ (can only fund innovation b's phase p if it's previous phase has already been successfully completed Sum over conditions C of $Z_c$ investments<overall budget Minimum gap for phase p<=$X_p$<=maximum gap for phase p, ∀ p $Y_b$<=total number of allowed parallel reviews FIG. 5 illustrates an exemplary computer system upon which examples of the disclosure can be implemented. The partners 577, 578, 579, 580, 585, 582, 590 and 595 can represent various health-related organizations and investors who can supply historical data as well as real time data on drug development and approval.

Policy decision-makers can explore policy decisions based on a variety of scenarios that are modeled in real time using advanced computational methods. Data can flow in and out of this computational analytic stack 570 in real time, and in this way interdependencies that will impact the innovation marketplace can be reviewed in simulated form prior to taking action. This pure form of computational synthesis and pre-exploration of intertwined factors and feedback vectors in a virtual environment allows for the creation of a biomedical innovation datametrics dashboard that governmental organizations can utilize to assess the impact that policy can have upon private research and development.

In addition, the simulation described above allows for the use of parallel computing to perform a minimization activity so as to identify satisficing solutions through the use of any one of a number of cognitive heuristics. It is envisioned that many such methods can be inserted into this functionality. Through searching multidimensional decision space, as powered by real and imputed data, the available alternatives can be screened until a predefined acceptability threshold is met. In this manner, it will be possible to leverage the power of computation to perform a valuable analysis that could not be accomplished by hand owing to the requirement that information be continuously synthesized and distributed among the computational nodes.

As illustrated in FIG. 5, industry partners 577, 578, 579, 580, 585, 582, 590 and 595 (biopharma, universities and research institutes) can upload historical data and evaluate simulation data in real time by communicating with the simulation system 570 from external computing devices 505.

Simulation system 570 can include 3 separate components which can be implemented on one or more computing devices. Simulation system 570 can include a partner engagement zone 510, a trusted computing zone 550 and an analytics zone 560. Each zone of the computing system 570 can be firewalled from one another so as to prevent unauthorized access to any one zone. The simulation system may also interact with public data available in various external sources 575. Public data in a variety of formats is downloaded from the public internet and other sites (CDC, WHO, etc.) on public health so as to provide information to the simulation system.

Partner engagement zone 570 can have an inbound area component 515 that can receive data to various external partners 505, an outbound area 520 that can transmit data to various external entities such as the external partners 505 and external information sources 575, and collaboration zone 525 that can facilitate collaboration amongst the partners 505.

Trusted computing zone 550 can facilitate real time updating by receiving data received by inbound component 515 and data from the simulation component 560, and send any updated data in real time to outbound component 520.

The biometric innovation datametrics dashboard analytics component 260 can include one or more computing devices in which the simulation described in FIGS. 1-4 can be implemented.

The biomedical innovation datametrics dashboard described above can be implemented through the use of various modules described in detail below that can interface with one another to help ensure that policy decision-makers and other stakeholders can decide on a combination of policies that best incentivizes private sector biomedical innovation in order to achieve a satisfactory set of outcomes, which may include, but is not limited to, reductions in DALYs, healthcare costs, increases in industry NPV, and improved clinical trial quality as described above. The modules and systems described below can be used to implement the biomedical innovation datametrics dashboard above, or alternatively can represent an additional embodiment of a biomedical innovation datametrics dashboard.

Figure 6:
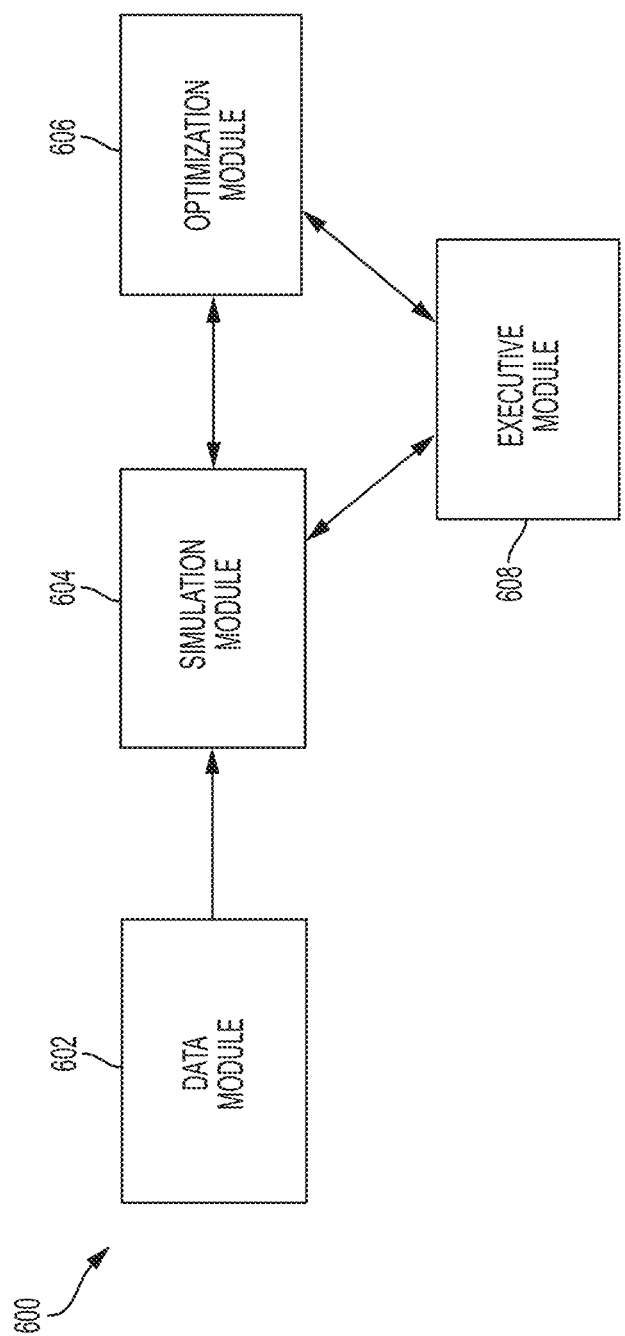
FIG. 6 illustrates an exemplary biomedical datametrics simulation system according to examples of the disclosure.

FIG. 6 illustrates an exemplary biomedical innovation datametrics dashboard according to examples of the disclosure. The system 600 can include four separate modules that interact with one another to execute simulations and can facilitate user interaction with creating and running simulations on the system. The system 600 can include a data module 602, a simulation module 604, an optimization module 606 and an executive module 608.

The Data Module 602 (described in further detail below) can import data from real-world data sources—including, but not limited to, clinical trial data, demographic data, and budgetary constraints—and can use the data to infer model parameters.

The Simulation Module 604 (described in further detail below) can perform simulations of the biomedical innovation ecosystem using parameters inferred from the Data Module 602, constraints and objectives specified via the Executive Module 608, and policy decisions specified by the Optimization Module 606 or the Executive Module 608. This may entail, but is not limited to, defining models of the following: policy options, budget allocations, private sector response to policy changes, the biomedical innovation pipeline, the healthcare delivery system, disease prevalence, and population dynamics.

The Optimization Module 606 can include interactive multi-objective optimization algorithms, which solicit feedback from human decision-makers via the Executive Module 608 and utilize predictions from the Simulation Module 604 in order to identify a set of policy decisions that best achieves multiple competing objectives and desired outcomes while satisfying the specified constraints.

The Executive Module 608 can include an interface through which human decision-makers can specify constraints and objectives to the Simulation Module 604, provide feedback to the Optimization Module 606, and view visualizations to compare and illustrate the predicted impact and outcomes of policy decisions.

The system 600 can be configured to include a set of features designed to address the challenges of multiple-criteria decision-making in the biomedical innovation domain, including but not limited to: using a simulation to model the biomedical innovation pipeline and predict the impact of policy decision on the biomedical innovation pipeline; infer model parameters in real-time using data from existing data sources; leverage feedback from a human decision-maker to more effectively traverse the solution space and seek a Pareto-optimal solution that achieves at least a satisfactory outcome for each objective. Each of these features are described in further detail below.

Figure 7:
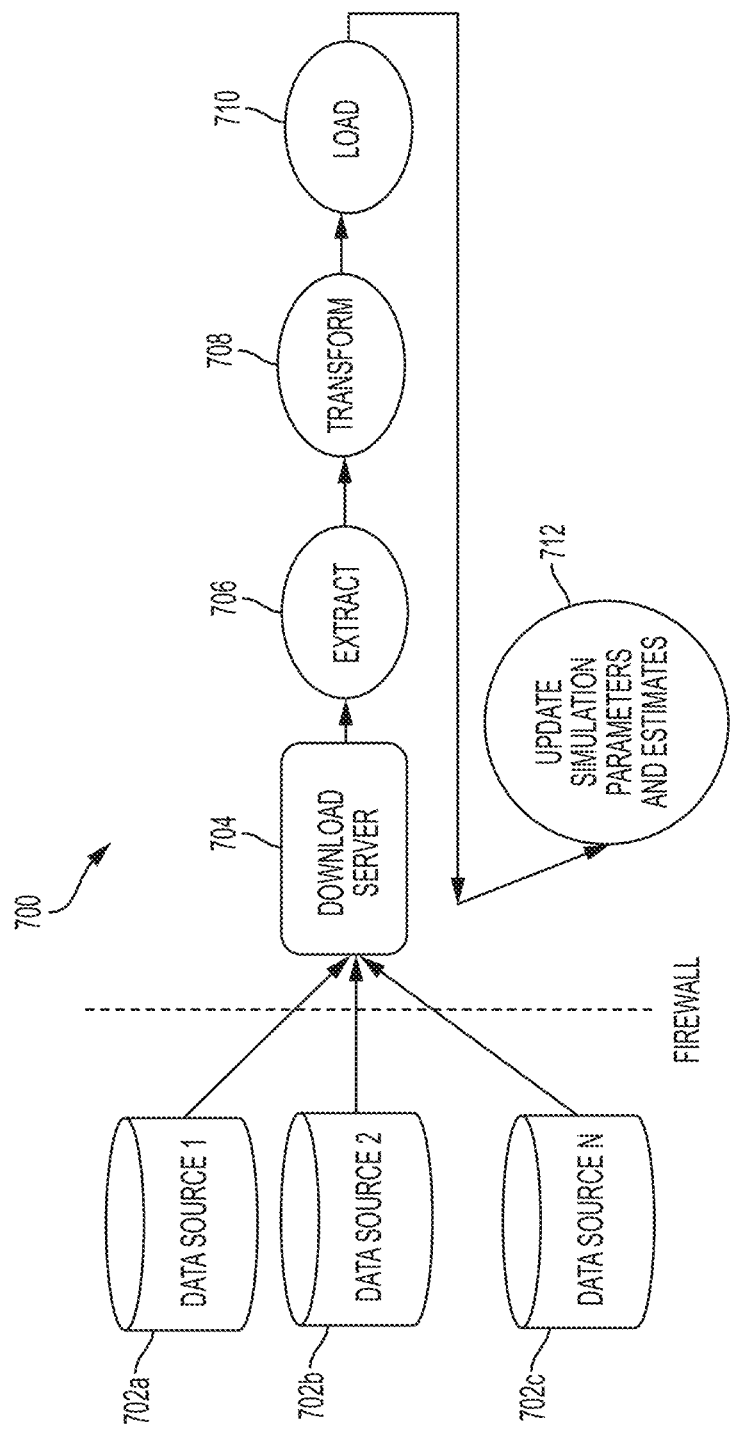
FIG. 7 illustrates an exemplary data module according to examples of the disclosure.

FIG. 7 illustrates an exemplary data module according to examples of the disclosure. The Data Module 700 can connect (via various network such as the internet or file transport protocol (FTP) networks) to several public and proprietary data sources. Data derived from these sources can be transformed to initialize key parameters used in the Simulation module. Data sources utilized can include, but are not limited to, clinical trial data, population growth statistics, population demographics, disease statistics, capital costs, time requirements, and discount rates.

Clinical trial data can describe the clinical trial pipeline by innovation type (biologic/drug/device/vaccine/diagnostic, etc.), target condition (breast cancer, glaucoma, etc.), research phase (Phase I, Phase II, Phase III, etc.), and expected duration. Parameters such as phase durations, costs, and success probability can be estimated for simulating future clinical trials.

Data from health organizations, government agencies, and literature sources can be used to initialize a base simulation population and disease attributes (prevalence, incidence, and mortality) subdivided by demographic categories including, but not limited to, race/ethnicity, sex, geography, education, and income. While only general estimates for each simulation parameter may be required, increasingly granular data sources and parameters can be incorporated to evaluate current and predict future health disparities. Industry data may include, but is not limited to, historical investment amounts in the different sectors of the biomedical innovation system, discount rates, and capital costs.

The user may select and update one or multiple data sources 702a-c upon starting the simulation system 600 of FIG. 6. If multiple data sources are available for the same purpose (e.g., population health data from CDC and WHO), a user may specify which dataset(s) to use. In the event a demographic-specific parameter is not available, it is estimated based on existing and available data.

Data module 700 can include a download 704 that can receive data via a network from various data sources 702a-b. Once the data is downloaded by the download server 704, extraction module 706 can process the received data and extract out the desired data to be used in the simulation. Transform module 708 can transform the extracted data into a format that is usable by the simulation. Since data sources 702a-c can be transmitted to the data module 700 in a plurality of formats, the transform module can ensure that the data sources are all loaded into the simulation using a common data format that the simulation can interpret and manipulated. The load module 710 can execute the loading of the transformed data to the simulation module (described below). Finally update module 712 can update simulation parameters and estimates for use in the simulation based on any new data received from data sources 702a-c as well as any inputs provided by the user of the simulation system.

A key challenge of the simulation system is to model how the private sector will respond to government policies. The output of the private sector response model from the Simulation Module can be compared to input from private sector organizations to hypothetical policies. As policies are implemented, data of the actual response to government policies can be added to help calibrate the private sector response module.

The evolving innovation pipeline of what clinical trials are started and stopped early can serve as private sector response to both macro-economic, environmental factors (cost of capital, United States and global growth, and population health trends, disease threats and prevalence) as well as the policies being implemented.

In addition, private sector organizations can login to the simulation system and indicate their potential response to various government policies.

The goal is to create a feedback loop for the model to be updated and calibrated with each addition of innovation pipeline data and/or hypothetical responses from the private sector organizations. This would be semi-automated—with data ingestion and parameter adjustment and then human modelers/programmers possibly making adjustments to the model as new features emerge.

Figure 8:
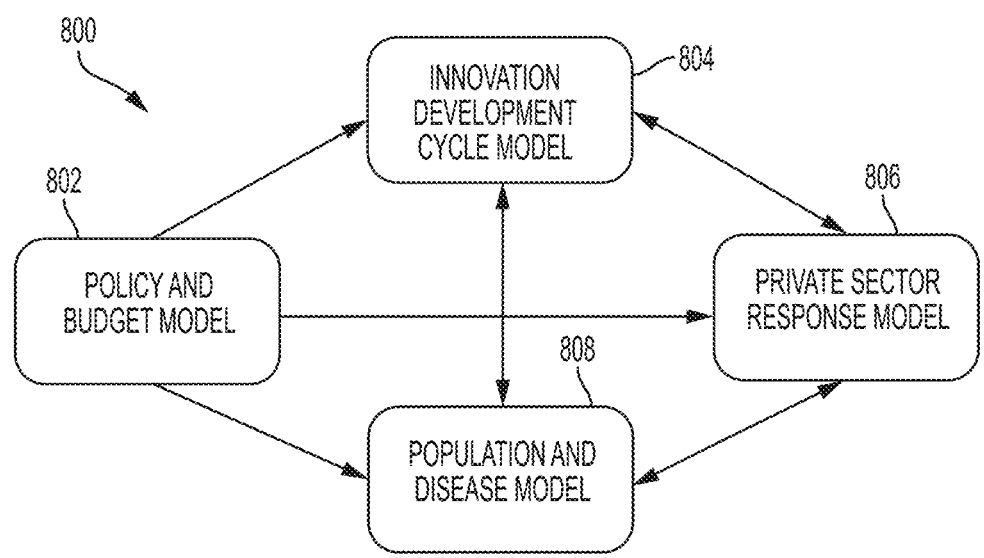
FIG. 8 illustrates an exemplary simulation model according to examples of the disclosure.

FIG. 8 illustrates an exemplary simulation model according to examples of the disclosure. The Simulation Module 800 may use, but is not limited to, Bayesian inference, compartmental models, and Monte Carlo simulation to predict the likely outcomes of potential policy scenarios. Key metrics outputted from the model for scenario comparison and analysis include, but are not limited to, changes in disease burden, treatment costs, and innovation NPV.

The Simulation Module 800 can integrate several distinct models, each comprised of multiple components, including, but not limited to: a Policy and Budget (PB) model 802, a Private Sector Response (PSR) model 806, an Innovation Development Cycle (IDC) model 804, and a Population and Disease (PD) model 808. Each individual model can simulate a key component of the overall biomedical innovation ecosystem. By using a modular, compartmental approach, individual model components can be substituted with increasingly complex models in order to more accurately represent innovation development behaviors. While some models may be motivated by or borrowed from existing literature, the linking and interaction among the models provides a novel, holistic approach to analyzing the effects of policy change on the biomedical innovation ecosystem.

The PB model 802 can interact with the Executive Module 608 to allow human decision-makers to specify policy decisions, budget allocations, and other parameters and constraints. The policy changes included within the PB model 802, but not limited to, are National Institute of Health (NIH) budget allocations, total NIH budget, phase cost adjustments, phase duration adjustments, Federal Drug and Food Administration—Centers for Medicare and Medicaid (FDA-CMS) parallel reviews, cost reimbursements, eligibility criteria for reimbursements, private challenge prizes, and clinical trial quality adjustments.

Higher budget allocations for a specific disease can result in more basic research and consequently, more successful innovations entering the market for that disease. Phase cost and phase duration adjustments are macro parameters that can affect the money and time required for developing biomedical innovations. These two parameters can influence the calculation of an innovation's NPV and the rate at which innovations progress through the innovation development cycle. FDA-CMS parallel review can be a specific policy that can be implemented and reduces the time required for innovation to pass through the FDA and CMS review stages of the innovation development cycle. Cost reimbursements, eligibility criteria for reimbursements, and private challenge prizes can be policies that can help promote innovations in diseases that does not typically attract private industry interest. Clinical trial quality adjustments modify the probability of an innovation successfully progressing from one stage to the next in the innovation development cycle.

Figure 9:
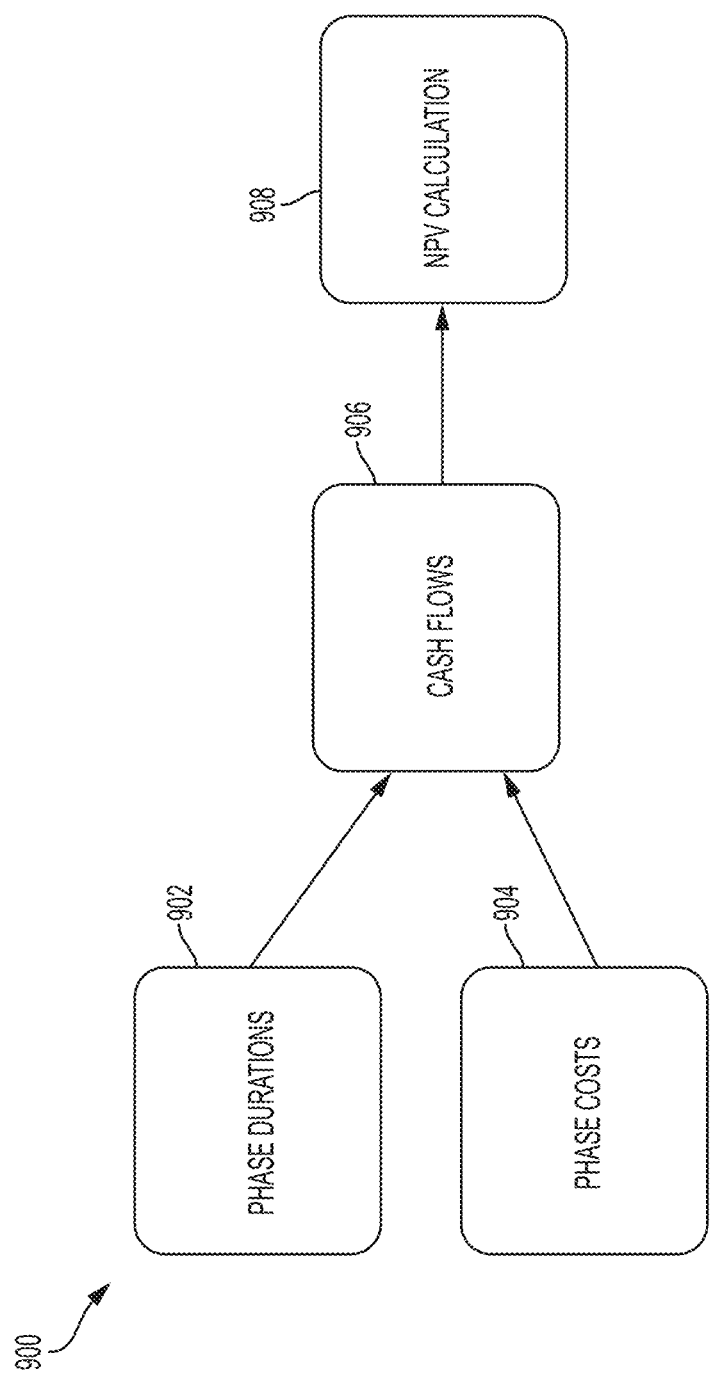
FIG. 9 illustrates an exemplary policy and budget model according to examples of the disclosure.

FIG. 9 illustrates an exemplary policy and budget model according to examples of the disclosure. The policy model 900 can include phase duration data 902, phase cost data 904, and cash flows model 906 that are then used by the NPV calculation model 908 using the examples and embodiments described above.

The PSR model 806 can simulate how the private sector changes its investment behavior in response to different policy scenarios and how those behavioral changes influence the development of biomedical innovations. Although private sector investment behavior is highly complex, the PSR model attempts to approximate this behavior using a combination of, but not limited to, NPV and market competition in creating a risk profile for a given innovation. Go vs. No-Go decisions on continuing the development of an innovation are made based on these calculated profiles. Innovations with an unfavorable risk typically have a negative NPV (unlikely to be profitable) with intense competition (many innovations for the same disease), while those with a more favorable profile have a positive NPV with less competition.

The PSR model 806 can calculate a risk profile for each innovation within the biomedical innovation pipeline. This profile is effectively a time-weighted NPV adjusted for the presence of competition, where innovations with a favorable profile (positive NPV) are continued and those with an unfavorable profile (negative NPV) are discontinued in the pipeline. Additional factors in calculating the risk profile can be included should there be a need for a more complex model.

For each innovation, the NPV can be calculated based on the expected profits, potential cash flow from challenge grants, the costs and time required for development, and an appropriate discount rate. Profits are adjusted for the presence of competition by reducing the potential obtainable market share based on the number of competitors. The calculation of NPV can be expressed as:

$$NPV(i, N) = \sum_{t=0}^{N} \frac{R}{(1+i)^t} \quad [1]$$

Where t denotes the time period of cash flow, N denotes the total number of time periods, i denotes the discount rate, and $R_t$ denotes the cash flow for period t. Alternatively, the Expected Present Value (EPV) can be calculated over multiple scenarios for a portfolio of innovations. Similarly, measures such as risk-adjusted NPV can be calculated to penalize highly undesirable outcomes such as large losses.

At each simulation time step, NPV and risk profiles can be recalculated based on changing market conditions, and innovations with unfavorable risk profiles are discontinued. Market conditions can change depending on new innovations entering the pipeline, resulting in increased competition, and older innovations' patents expiring, resulting in less competition. Moreover, the total treatable disease populations can change over time as the total population grows and disease prevalence changes.

For each simulation time step, each innovation can have its NPV calculated in isolation where the innovation estimates the future market share and disease population based on current treatments available, but not accounting for other innovations in the pipeline. If an innovation has a positive NPV, then it can have some probability of being funded. This probability of funded can based on a mapping function to NPV, where negative NPV has a 0 probability of being funded and a very high NPV approaches a 1.0 certainty of being funded. Based on these funding probabilities, the future pipeline can be calculated using the probability of success for each innovation phase to estimate the number of innovations for a given market and the potential market share. Based on the new estimate of market share, the NPVs are re-calculated for each innovation and the probability of funding is re-calculated. (This set of calculations can be calculated two or more times until the simulation converges within a defined amount.) If government policies create incentives (parallel review, etc.) that make a particular type of innovation more favorable to develop, then more private sector private sector organizations may respond with development, which may result in increased competition and reduced market share and NPV.

Figure 10:
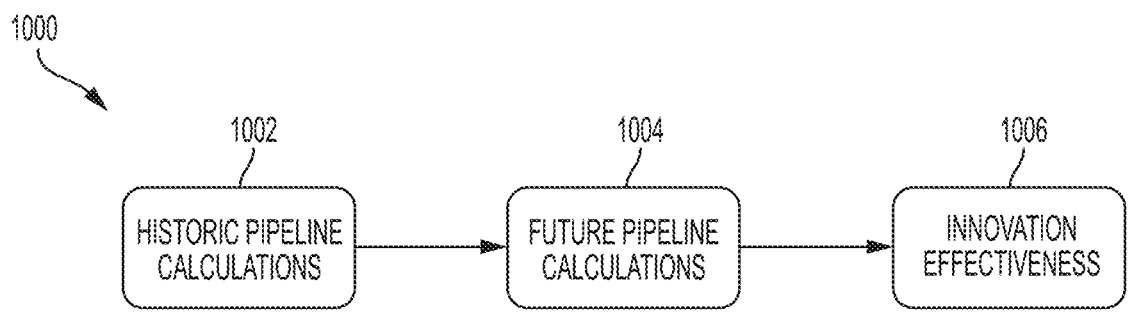
FIG. 10 illustrates an exemplary private sector response model according to examples of the disclosure.

FIG. 10 illustrates an exemplary private sector response model according to examples of the disclosure. The model 1000 can include the historic pipeline calculations 1002, the future pipeline calculations 1004 and the innovation effectiveness calculations 1006 described above.

The innovation development cycle (IDC) model 804 can simulate the process, in which a biomedical innovation progresses through the various stages of the development cycle, and creates a schedule of biomedical innovations that influences health outcomes and private sector responses. The types of biomedical innovations currently included, but not limited to, in the IDC model are drugs, biological agents, medical devices, and vaccines. While the exact development cycle an innovation undergoes depends on the innovation type and targeted disease, the development cycle for all innovations can be represented or approximated by the following stages: Basic Research, Basic Research Gap, Targeted Research, Targeted Research Gap, Preclinical Research, Preclinical Research Gap, Phase I, Phase I Gap, Phase II, Phase II Gap, Phase III, Phase III Gap, FDA Approval, FDA Gap, CMS Approval, Market Entry, and Patent End. A phase of market end can also be considered if one desires to model potential obsolescence where a drug/device etc. may no longer be part of the standard of care in some future time.

The IDC model 804 can utilize a discrete event simulation approach for projecting the development of biomedical innovations. Each innovation can be represented as a discrete entity that resides in each stage for some amount of time and then transitions to the next stage within the development cycle based on innovation type and disease specific stage residence times and transition probabilities derived from literature and industry sources. Thus, each innovation's transition can be represented by a Markov model where, only the current state of the innovation can be significant and not what series of state transitions happened before. The innovation pipeline for the IDC model 804 can be initialized using clinical trial and other data that provide information on past, current, and planned clinical trials. Furthermore, the initial number of innovations in the stages from Basic research through Preclinical Research Gap can be linearly approximated based on the clinical trial data.

For each simulation time step, if an innovation has remained within a stage for the specified residence time then it can have some probability of successfully transitioning to the next stage. However, if the entity fails to transition successfully then it can be removed from the innovation pipeline. New innovations are introduced into the pipeline at the basic research stage based on the budget allocation. Typically, more innovations are introduced for diseases that received a higher budget allocation.

When an innovation reaches the Market Entry stage, it can be assigned an innovation effectiveness factor for reducing disease mortality rates, incidence rates, and disability weightings. All innovations that reach the Market Entry stage can be passed into the PD model 808 to simulate their effect on population health and disease burden. Once an innovation reaches the patent end stage, then the treatment cost associated is reduced by a user-specified multiplier.

Figure 11:
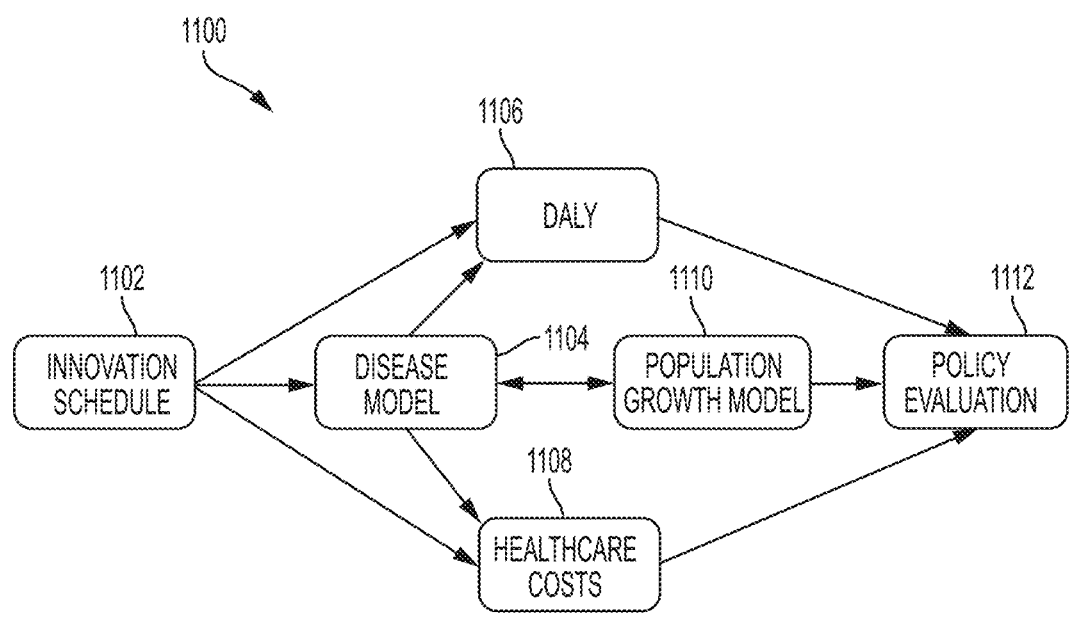
FIG. 11 illustrates an exemplary innovation pipeline model according to examples of the disclosure.

FIG. 11 illustrates an exemplary innovation pipeline model according to examples of the disclosure. The innovation pipeline model 1100 can include an innovation schedule 1102, a disease model 1104, a DALY model 1106, and healthcare costs model 1108, and population growth model 1110 and a policy evaluation model 1112 as described above.

The population and disease (PD) model 808 can forecast future population distributions and disease burden based on inputs from other model-components and data sources describing population growth statistics and disease characteristics. More specifically, the PD model 808 can forecast population distributions that can be categorized by—but not limited to—disease, age, sex, and demographic features (e.g. ethnicity/race, socioeconomic status, and education). The model can also calculate metrics such as DALY, mortality, prevalence, and treatment costs for quantifying the economic and health burden for each disease.

The PD model 808 can allow for a highly granular analysis, which can enable policy makers to identify specific population groups that may be at high-risk or underserved. By inputting multiple scenarios of policy change, policy makers can quantitatively assess and compare each scenarios' impact on disease burden for specific populations over time.

The PD model 808 can utilize a cohort-component method to forecast future population distributions and disease burdens. A cohort can be defined as a population that share similar features and has its own set of assumptions to be used in producing forecasts. The PD model 808 can be subdivided into two parts, the population growth model and disease burden model, which are described in more detail below.

Future population distributions can be forecasted based on an initial base population in from a given time period. For instance, Jan. 1, 2012. In this model, population changes can be predicted separately for each cohort, in which changes are driven by cohort-specific assumptions and parameters. Therefore, the model can require separate inputs of birth, mortality, and net immigration rates for each cohort defined. Cohort mortality rates can be adjusted during each simulation time step to account for the effect of new biomedical innovations on disease burden. Birth and net immigration rates can be assumed to be approximately equal throughout the course of the simulation, but models for projecting future birth and net immigration rates can be included into the PD model if needed.

For each simulation time step of a year, each cohort can advance by one year of age after applying cohort-specific adjusted-mortality rates and net international migration rates. A new birth cohort can be added to the population by applying cohort-specific birth rates to the female population. The cohort component method for forecasting population changes can be expressed as:

$$P_{t,c} = P_{t-1,c} + B_{t-1,c} - D_{t-1,c} + M_{t-1,c} \quad [1]$$

Where t denotes a time interval, c denotes a cohort, P denotes the size of the population, B denotes the number of births, D denotes the number of deaths, and M denotes the net migration.

Similar to the population growth model, the disease model can forecast future disease population distributions based on an initial disease base population. For each disease and cohort, parameters for mortality rates, incidence rates, disability weighting, and DALY can be required as inputs into the model.

For each simulation time step, changes in the disease population distribution can be calculated based on the adjusted mortality and incidence rates. While more complex models, if available, can be used to estimate disease deaths and incidences, a linear model can be used by default to estimate the population change. For each cohort, the number of new disease cases can be calculated by multiplying the age-specific incidence rates by the number of healthy individuals. The cohort component method for forecasting disease population changes can be expressed as:

$$P_{t,c} = P_{t-1,c} - D_{t-1,c} + I_{t-1,c}$$

Where t denotes a time interval, c denotes a cohort, P denotes the size of the disease population, B denotes the number of births, D denotes the number of deaths, and I denotes the number of new incidences of disease.

At each simulation time step, the mortality and incidence rates are adjusted to reflect the effects of new biomedical innovations entering the market. Currently, effects of biomedical innovations are captured via applying a cumulative product to the initial rate. Each biomedical innovation has its own effectiveness factor between 0 and 1 for influencing mortality rate, incidence rate, and disability weighting factor, and thus, the net effect of all biomedical innovations on a given disease parameter is expressed as:

$$p_{net} = p_{init} * \prod_{n=1}^{N} b_n$$

Where $p_{net}$ denotes the effective parameter, $p_{init}$ denotes the initial parameter, N denotes the total number of biomedical innovations in effect, and $b_n$ denotes the biomedical innovation effect on the parameter. This approach can utilize the simplifying assumption that each innovation's effectiveness is incremental and multiplies to reduce the disease burden (DALY, costs, etc.). A more sophisticated approach could be used that estimates the $p_{net}$ factor as a function of the innovations $b_1$ to $b_n$, some of which may be multiplicative or additive, or have some other relationship.

Figure 12:
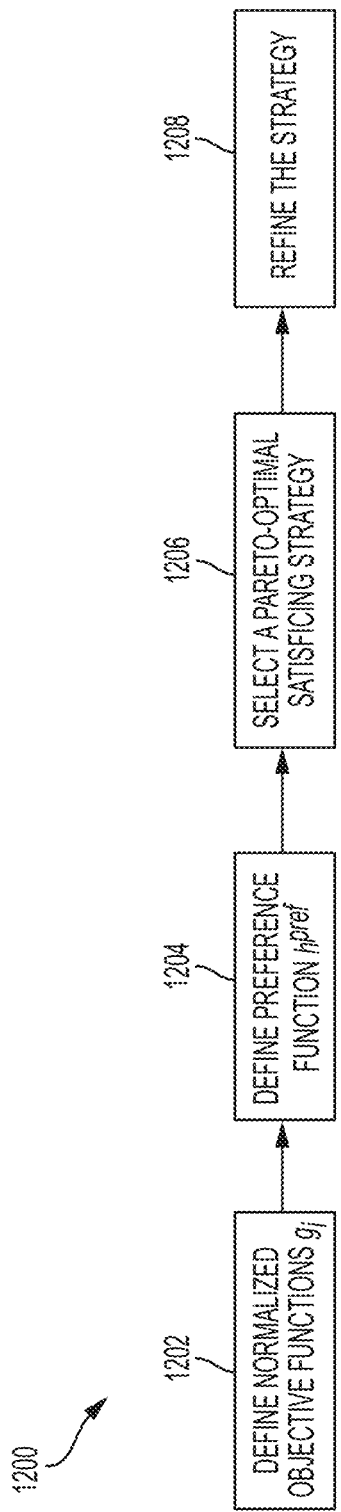
FIG. 12 illustrates an exemplary high-level method to optimization according to examples of the disclosure.

The Optimization Module 606 can include a sequence of procedures (the Interactive Multi-Objective Decision-Making (IMOD) Algorithm, or the "algorithm") designed to assist a decision-maker or decision-making team (the "user") in selecting a satisficing strategy to a multi-objective optimization task (the "solution") in accordance with the user's preferences. It can be assumed for the purposes of this algorithm that the user can represent the combined needs and preferences of all stakeholders in the decision-making process; this could, for example, be implemented via consensus voting for each user prompt. FIG. 12 illustrates an exemplary high-level method to optimization according to examples of the disclosure. The method 1200 can include four main steps: (1) define a normalized objective function for each objective illustrated at step 1202; (2) define a preference function over the strategy space illustrated at step 1204; (3) select a satisficing strategy based on user preferences illustrated at step 1206; and (4) refine the strategy via small perturbations illustrated at step 1208. The steps are described in greater detail below. The key features of the method can include, but are not limited to: Incorporating a priori, a posteriori, and interactive methods for multi-objective optimization; employing a hybrid method in which human interaction is used to infer parameters of a preference function in a way that is intuitive for the user; and simultaneously balancing multiple competing objectives by returning a Pareto-optimal strategy while satisfying user-specified minimum constraints A strategy is specified by a vector $x=(x_1, \ldots, x_n)$ corresponding to the values of n input parameters, such as policy choices and budget allocations. Let X denote the set of all strategies. The simulation function $f^{sim}$ maps each strategy $x \in X$ to its output profile $f^{sim}(x)=(f_1^{sim}(x), \ldots, f_m^{sim}(x))$ corresponding to the projected outcomes of the m objectives upon running the Simulation Module with strategy x. For strategies x, $y \in X$, x is said to dominate y if ($\forall$ i) $f_i^{sim}(x) \geq f_i^{sim}(y)$ and ($\exists$ i) $f_i^{sim}(x) > f_i^{sim}(y)$. A strategy $x \in X$ is said to be Pareto-optimal if ($\not\exists$ $y \in X$) such that y dominates x. The threshold vector $\theta=(\theta_1, \ldots, \theta_m)$ specifies the minimum acceptability threshold required to satisfy each of the m objectives.

A strategy $x \in X$ is said to be satisficing if its output profile satisfies all objectives, i.e. ($\forall$ i) $f_i^{sim}(x) \geq \theta_i$. Let S denote the set of all satisficing strategies. The normalized objective function $g_i$ maps satisficing strategies $x \in S$ to values in [0,1], increasing monotonically with $f_i^{sim}(x)$. The preference function $h^{pref}$ maps satisficing strategies $x \in S$ to values in [0,1], such that x dominates $y \Rightarrow h^{pref}(x) \geq h^{pref}(y)$.

Step 1202 is described in detail below. In standard optimization problems, an objective function can measure the quality of a proposed solution. In multi-objective optimization, there can be an objective function for each objective. The Simulation Module 600 can provide a way of evaluating the quality of a solution with respect to the specified set of target objectives. i.e. $f^{sim}(x)$. In the context of satisficing, solutions are only feasible if a minimum acceptability threshold $\theta_i$ is satisfied for every objective i. Therefore, we define a new set of objective functions $g_i$ only over the domain of satisficing strategies, mapping each satisficing strategy to a value in [0,1], where $g_i(x)=0$ if $f_i^{sim}(x)=\theta_i$, the minimum possible value for a satisficing strategy; $g_i(x)=1$ if $f_i^{sim}(x)=\Omega_i$, the maximum value achieved by any satisficing strategy; and with the requirement that $g_i(x) > g_i(y)$ if $f_i^{sim}(x) > f_i^{sim}(y)$.

The method at step 1202 can begin by prompting the user for the minimum acceptability thresholds $\theta_i$ via the Executive Module 608. Next, the algorithm can estimate the maximum feasible values $\Omega_i$ by independently performing single-objective optimization on each objective, with the constraint that solutions must correspond to satisficing strategies. The specific optimization technique used is outside the scope of the current invention; some commonly-used methods are gradient descent, genetic algorithms, and simulated annealing Once the minimum and maximum values of $f_i^{sim}(x)$ have been determined for each objective i, the normalized objective function $g_i$ can be as follows:

$$g_i(x) = \frac{f_i^{sim}(x) - \theta_i}{\Omega_i - \theta_i}.$$

That is, $g_i$ is a monotonically increasing linear function that normalizes $f_i^{sim}$ over the feasible range $[\theta_i, \Omega_i]$. This normalization can enable the method to more easily compare objectives to one another, which is done in the next step. If no feasible satisficing solution can be found with the thresholds set, then the user algorithm would inform the decision maker(s) that no feasible solution was found and direct them to re-negotiate the thresholds and adjust.

Step 1204 is described in detail below. When multiple factors are involved in a decision, the decision-maker may give some factors stronger weight than others, leading the decision-maker to prefer some satisficing solutions over others. In the present invention, this is expressed through a preference function $h^{pref}$. Since it is assumed that if one strategy dominates another, the decision-maker will prefer the dominating strategy, we require that $h^{pref}$ respect dominating relationships. For the purpose of illustration, we consider a function of the following form:

$$h^{pref}(x) = \sum_i \gamma_i \cdot g_i(x),$$

With the constraint that $\Sigma_i |\gamma_i|=1$, where the parameters $\gamma_i \in [-1,1]$ provide a relative weighting among the objectives, with negative weights corresponding to objectives for which lower values are more desirable. This is only one possible form of the preference function, and the present disclosure is not limited to its use.

Once the user's preferences are captured in a preference function, the preference function can be used as the objective function in an automated optimization process. However, a decision-maker's preferences are often intuitive, and asking the user to specify them as a mathematical formula may be both daunting and confusing, likely leading to a preference function that does not accurately express the user's preferences.

An alternative to asking the user to specify a preference function explicitly is to infer their preferences based on feedback to more intuitive questions, a task sometimes referred to in the literature as preference elicitation. For the purpose of illustration, we consider a mechanism in which the user is presented with pairs of output profiles (i.e., candidate strategies), which may be chosen randomly or judiciously (e.g. to maximize discriminative power and/or based on history of previous candidate pairs and responses), and is asked to decide whether they prefer the first option, prefer the second option, or have no preference. The output profiles may but need not correspond to actual strategies, since here the goal is to infer the preference function, not to propose strategies (which will occur during steps 3 and 4). However, the output profiles must satisfy all objectives, since the preference function is only defined over satisficing strategies. This is only one possible mechanism for preference elicitation, and the present invention is not limited to its use.

Next, the method uses the feedback to infer the preference function, namely by inferring the $\gamma_i$ values. In particular, for each pair of output profiles $(x^{(j)}, y^{(j)})$ presented to the user, we derive an equation or inequality involving the $\gamma_i$. For the purpose of illustration, we provide the following derivation of the equation corresponding to a no-preference decision for the example mechanism described above, which can easily be modified for the case of an inequality:

$$h^{pref}(x^{(j)}) = h^{pref}(y^{(j)}) \Rightarrow \prod_i g_i(x^{(j)})^{\gamma_i} = \prod_i g_i(y^{(j)})^{\gamma_i}$$

$$\Rightarrow \prod_i \left(\frac{g_i(x^{(j)})}{g_i(y^{(j)})}\right)^{\gamma_i} = 1$$

$$\Rightarrow \log\left(\prod_i \left(\frac{g_i(x^{(j)})}{g_i(y^{(j)})}\right)^{\gamma_i}\right) = 0$$

$$\Rightarrow \sum_i \gamma_i \cdot \log\left(\frac{g_i(x^{(j)})}{g_i(y^{(j)})}\right) = 0.$$

Each equation or inequality defines a plane or half-space, respectively, in the m-dimensional space corresponding to possible $\gamma_i$ values. We also have the constraint that $\Sigma_i |\gamma_i|=1$ from above, which helps to bound the space.

Finally, the system of equations and inequalities is solved for the best-fit parameters $\gamma_i$. If the system does not have a unique solution, the algorithm could take a central point in the solution space (if multiple solutions exist) or choose $\gamma_i$ values that minimize error (if no exact solution exists).

This process may be repeated as desired (e.g. until information gain/discriminative power falls below a threshold, or until preferences can be predicted accurately).

Figure 13:
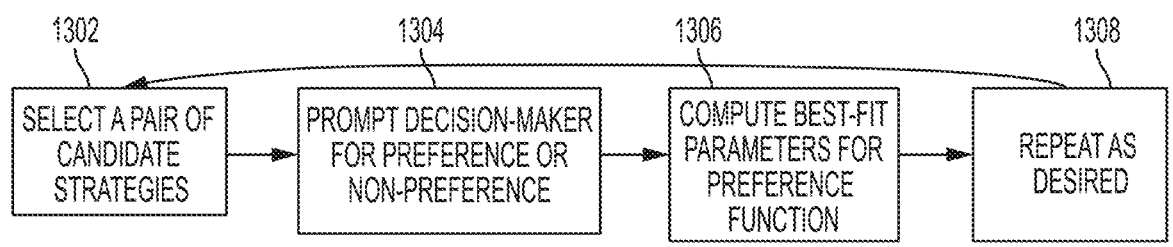
FIG. 13 illustrates an exemplary preference function step according to examples of the disclosure.

FIG. 13 illustrates an exemplary preference function step according to examples of the disclosure. At step 1302, the user is prompted to select a pair of candidate strategies as described above. At step 1304, the decision maker can be prompted for their preferences and non-preferences as described above. At step 1306, the best fit parameters for the preference function can be computed and finally at step 1308, the process can be repeated if desired.

Step 1206 is described in detail below. Now that the preference function $h^{pref}$ has been defined, the algorithm searches for highly-preferred strategies by performing single-objective optimization over the space of satisficing strategies, using $h^{pref}$ as the objective function.

Since $h^{pref}$ only specifies the trade-offs between objectives, there may be strategies that are substantively different yet have the same or similar preference score. In this case, the user may be presented with a representative sample of Pareto-optimal satisficing strategies and prompted to choose between them. For example, this could be done by running a genetic algorithm and presenting a subset of the resulting population with diverse genetic makeups.

Figure 14:
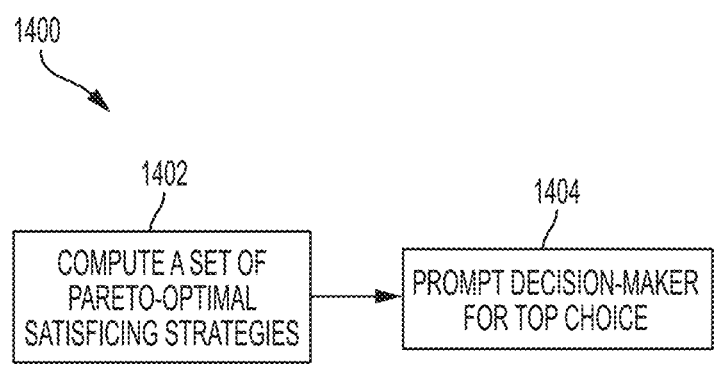
FIG. 14 illustrates a strategy selection step according to examples of the disclosure.

FIG. 14 illustrates a strategy selection step according to examples of the disclosure. The method 1400 of FIG. 14 can illustrate the process with respect to step 1206 of FIG. 12. At step 1402 a set of Pareto-optimal satisficing strategies can be computed. Once computed, at step 1404 the decision maker (i.e., the user) can be prompted to select their top strategy choice from the satisficing strategies computed at step 1402.

Step 1208 is described in detail below. The method can provide the user with an opportunity to refine the selected strategy. The user can be prompted to indicate whether each objective should be improved, could be relaxed, or is acceptable in its current state. The algorithm then attempts to perturb the currently-selected strategy in the direction of the user's indications. The best strategy found is presented to the user, who either selects it as the new current strategy or retains the previous strategy. The algorithm terminates when the user is satisfied with the currently-selected strategy, or when all local perturbations have been exhausted.

Figure 15:
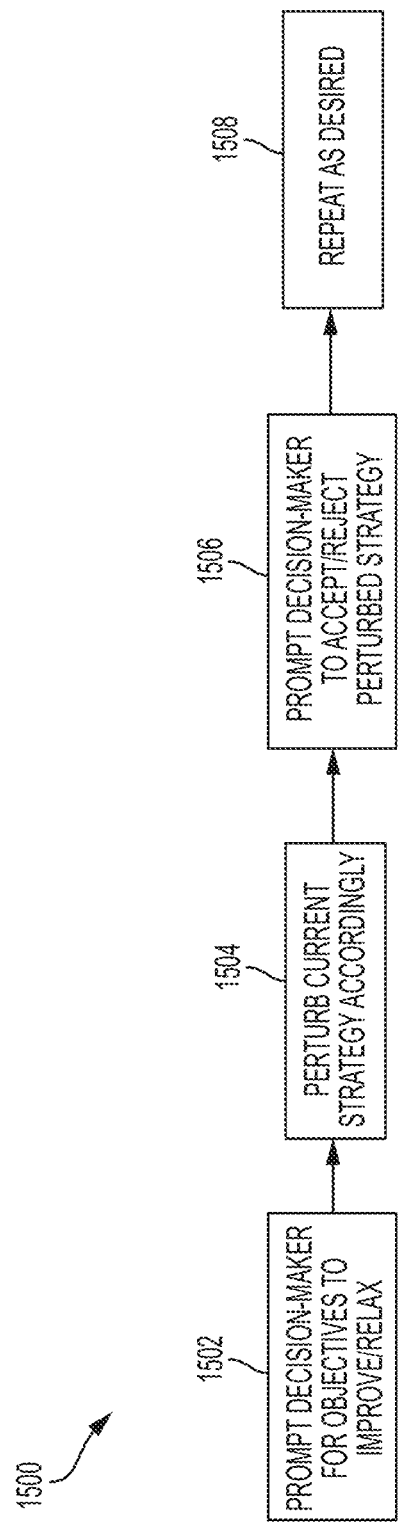
FIG. 15 illustrates an exemplary refining method according to examples of the disclosure.
Figure 16A:
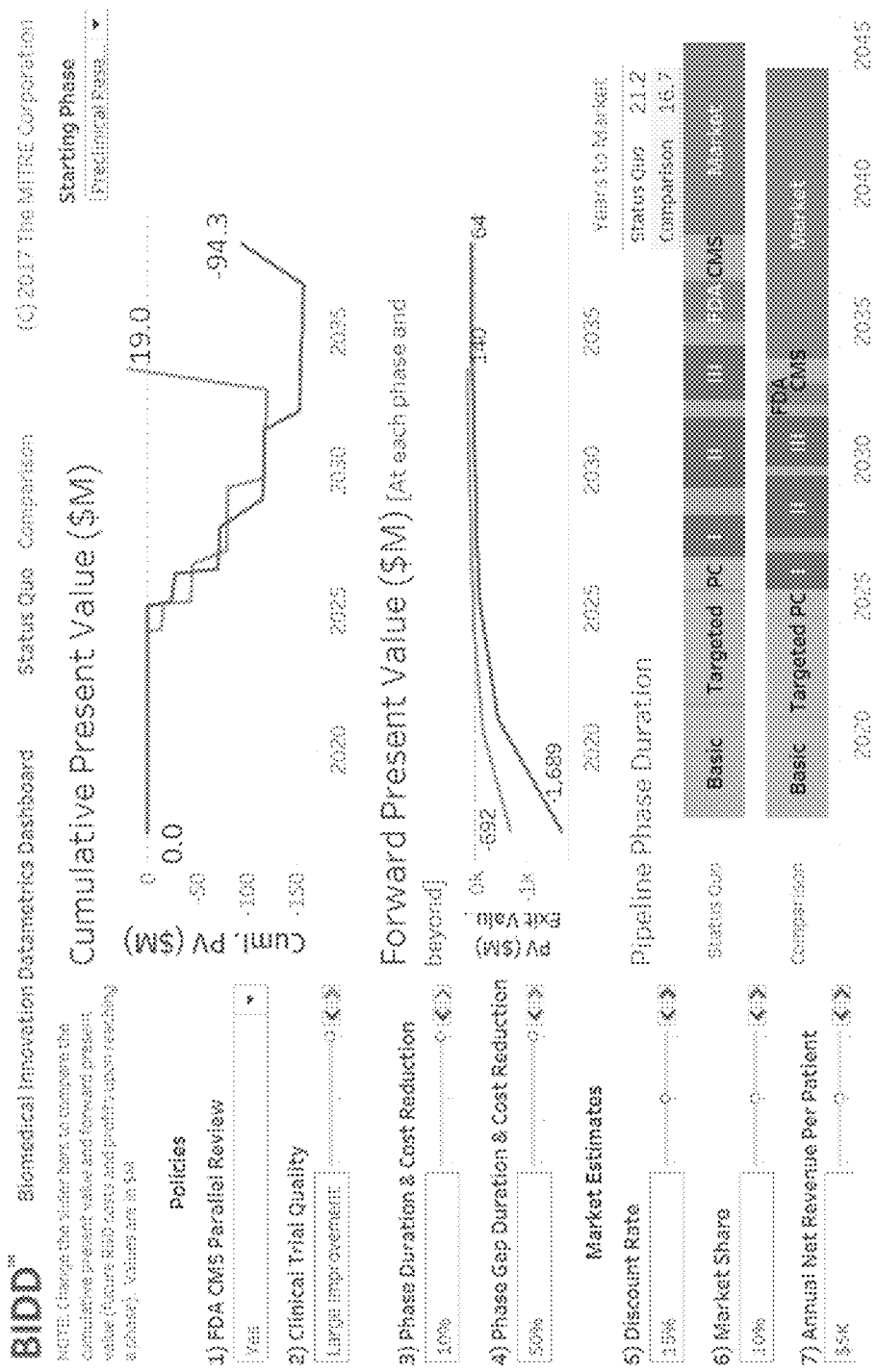
Figure 16D:
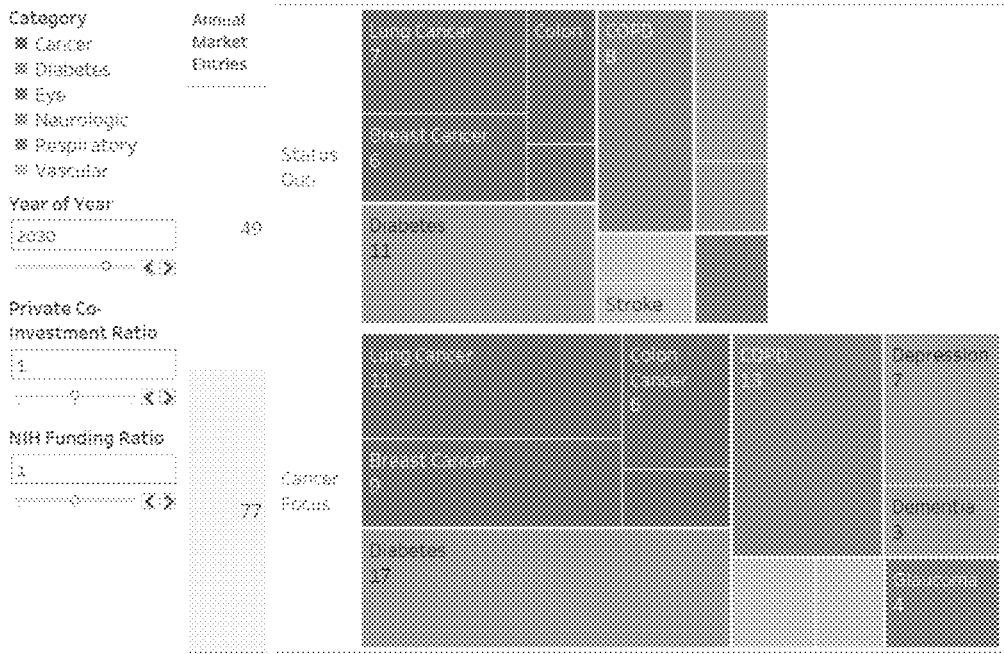
Figure 16E:
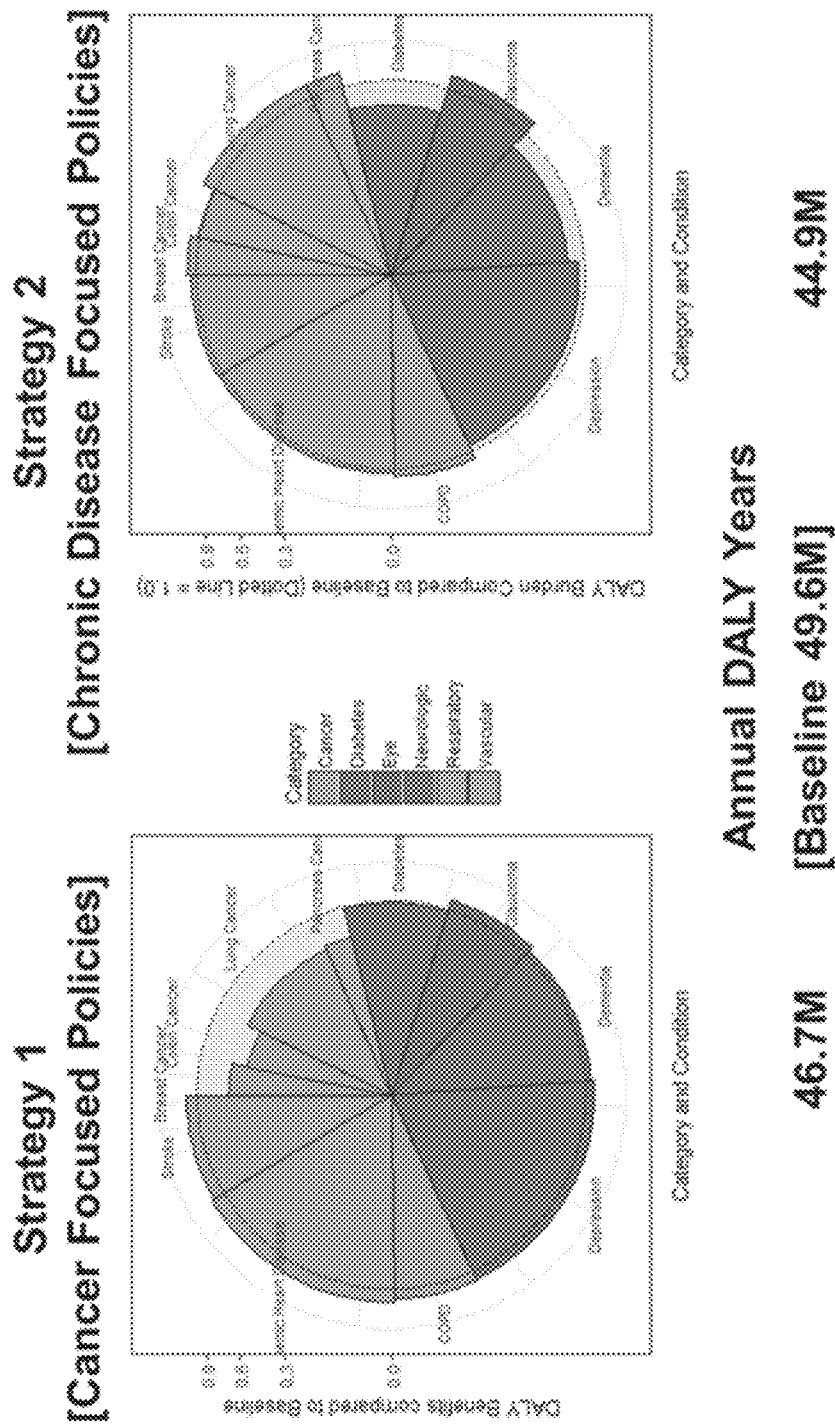

FIG. 15 illustrates an exemplary refining method according to examples of the disclosure. The method of FIG. 15 can illustrate the process with respect to step 1208 described in FIG. 12 above. In the method 1500, at step 1502 the decision maker can be prompted to provide objectives to improve the satisficing strategy selected in the prior step. At step 1504 the current strategy can be perturbed according to the objectives selected at step 1502. At step 1506, the user can be prompted to accept/reject the perturbed strategy. Finally, at step 1508, the process can be repeated if desired.

The system's 600 Executive Module may include, but is not limited to, three modes—Configuration mode, Exploration mode, and Optimization mode (discussed in detail below). Each mode can include interfaces between human decision-makers and the other modules of the present invention. As an example the Executive Module may include: an overview interface for directing the user to choose one of the three modes; an interface for selecting the data sets to be used (Configuration mode); an interface for defining objective functions and minimum acceptability thresholds (Configuration mode); an interface for viewing and modifying a strategy consisting of policy decisions and budget allocations (Exploration mode); an interface for visualizing the projected impact and outcomes of a strategy over time with detailed views of sub-outcomes (Exploration mode); an interface for selecting the range of policies to be considered for a potential strategy (Optimization mode); an interface for comparing two strategies and indicating a preference between them (Optimization mode); an interface for comparing multiple strategies and selecting one of them (Optimization mode); and an interface for perturbing a given strategy by indicating objectives to improve or relax (Optimization mode).

The overview interface for directing the user to choose a mode can allow for the user to choose between a configuration mode of the system, an exploration mode of the system, and an optimization mode of the system. The Executive module 608, in one example, can include an interface wherein the user is prompted to configure the Data Module 602 by selecting from existing data sets and/or importing new data sets. This interface can be used in Configuration mode. Additionally, an interface can be provided for allowing the user to define objective functions and minimum acceptability thresholds. In addition to the main objectives, including but not limited to, DALY, healthcare costs, industry NPV, and clinical trial quality, there can be additional objectives encouraging fairness or equity across or within objectives. This interface is used in Configuration mode.

In another example, an interface can be provided for viewing and modifying a strategy consisting of policy decisions and budget allocations. The user can be allowed to view and modify each component policy decision in the strategy and then re-run the simulation to predict the corresponding impact on the objectives. This interface can be used in Exploration mode. In another example, the Executive module 608 can provide an interface for allowing the user to visualize the projected impact and outcomes of a strategy over time.

In another example, an interface can be provided by the Executive module 608 that allows for the user to visualize the projected impact and outcomes of a strategy over time. The user can view an interactive dashboard to explore the projected impact over time for each objective and drill into details of the objectives (e.g. DALY reduction by condition, sex, race, age, or time period) by sub-objectives or combinations of interest (e.g. cancer disparities in minorities or chronic disease costs). In addition to seeing tables and charts showing the value of each objective and the range between minimal satisficing level and optimal level for each objective, the user may explore sub-objectives to look for equity and fairness for stakeholders or affected populations. This interface can be used in Exploration mode.

In another example, the Executive module 608 can provide an interface for selecting the range of policies to be considered for a potential strategy. For example, a decision-maker may want to adjust a policy (NIH Funding ratio) or one organization's policies to default values and then let the other policies be explored via the Optimization Module. This interface is used in Optimization mode. In another example, the user can be provided an interface for comparing two strategies and indicating a preference between them. The user can view both scenarios' policy components, objectives, and sub-objectives, and indicate whether they prefer one strategy, the other strategy, or are indifferent. This may include some or all of the functionality of the single-strategy interface, as well as additional functionality for comparing the two strategies. This interface can be used by Step 1204 of the method described above with respect to FIG. 12. in the Optimization Module 606. This interface can be used in Optimization mode. In another example, the Executive module 608 can provide an interface for comparing multiple strategies. This interface can be used in step 1206 of the method described with respect to FIG. 12 and in the discussion relating to Optimization Module. This interface can be used in Optimization mode 606. In another example, the Executive module 608 can provide the user with an interface for perturbing a given strategy by indicating objectives to improve or relax. The user can indicate one or more objectives to improve or relax, to find other neighboring solutions that may have an overall more favorable combination of objective values. This interface can be used by Step 1208 of the method described with respect to FIG. 12 in the Optimization Module 606. This interface can be used in Optimization mode.

To help decision makers compare among the hierarchical components of two scenarios, can use Spie charts (http://www.cs.huji.ac.il/~feit/papers/Spie03TR.pdf) to show comparisons between strategies for each objective. The spie chart can set the angle using one set of data and sets the radius a comparison set of data.

The executive model 608 can provide various dashboards to the user to help them visualize the results of the simulations and satisficing solutions. FIGS. 16a-e illustrates various exemplary dashboards displayed to a user according to examples of the disclosure.

In addition to biomedical innovation, the BIDD System could be applied to evaluate other health related policies, private sector actors, and objectives. For example, CMS Medicare and Medicaid alternative payment models could be evaluated to simulate how the private sector actors (hospitals, physician practice groups, insurers, etc.) respond to policy incentives, and search for satisficing solutions to multiple objectives, including fairness or equity objectives.

The simulation model described above can additionally include payment models policy simulations that model global payments, bundled payments, incentive payments, MACRA and future laws and policies, national health expenditure estimates that can include the impact of technology, including the value of accelerating biomedical innovation, co-morbidity cost estimates. Additionally, the simulation model can model improved treatments and incentives for the sickest, costliest payments.

Returning to the example of FIG. 8, the simulation model 800 can also include a clinical trial quality model. Clinical trial quality can be a key factor that may influence the probability of success of each clinical trial phase of a given innovation. In the BIDD system, clinical trial quality may also be considered an output objective for the decision maker. Clinical trial quality (including issuing of standards, training, incentives, etc.) can influence factors that lead to higher clinical trial quality, which can lead to more successful innovations entering the marketplace.

Figure 17:
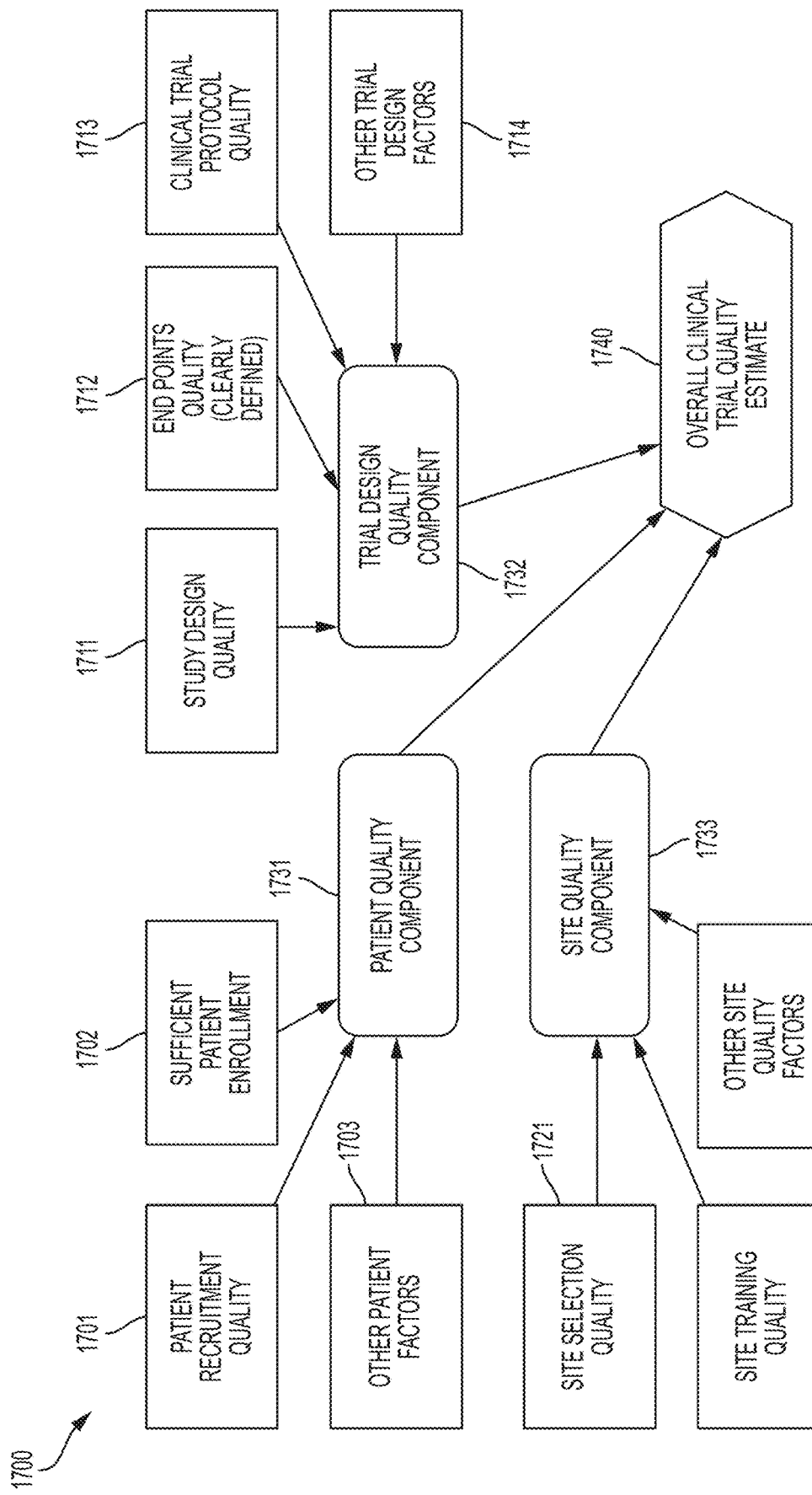
FIG. 17 illustrates a clinical trial quality model according to examples of the disclosure.

FIG. 17 illustrates a clinical trial quality model according to examples of the disclosure. The clinical trial model 1700 can include multiple quality inputs and can calculate component scores and provide an overall clinical trial quality estimate. The model 1700 can include inputs such as input 1701 (Patient recruitment quality), 1702 (sufficient patient enrollment) and 1703 (other patient factors) to produce a patient quality component score 1731. Patient quality component score 1731 can be calculated using a function of these patient quality input estimates. (E.g., a product function with each input ranging from 0 [lowest quality] to 1 [ideal quality].)

1711, 1712, 1713, and 1714 can estimate the study design quality, end points quality (clearly defined), clinical trial protocol quality, and other trial design factors, respectively. 1732 can be a trial design quality component score that can be calculated using a function of these patient quality input estimates. (E.g., a product function with each input ranging from 0 [lowest quality] to 1 [ideal quality].)

1721, 1722, and 1723 can estimate the site selection quality, site training quality, and other site quality factors, respectively. A site quality score component 1733 can be calculated using a function of these patient quality input estimates. (E.g., a product function with each input ranging from 0 [lowest quality] to 1 [ideal quality].)

1740 is an overall clinical trial quality estimate, which can be a function of the component scores of 1731, 1732, and 1733 (patient quality component, trial design quality component, and site quality component). (E.g., a product function with of each component score, which ranges from 0 to 1. Some components could be weighted more as desired.)

Figure 18:
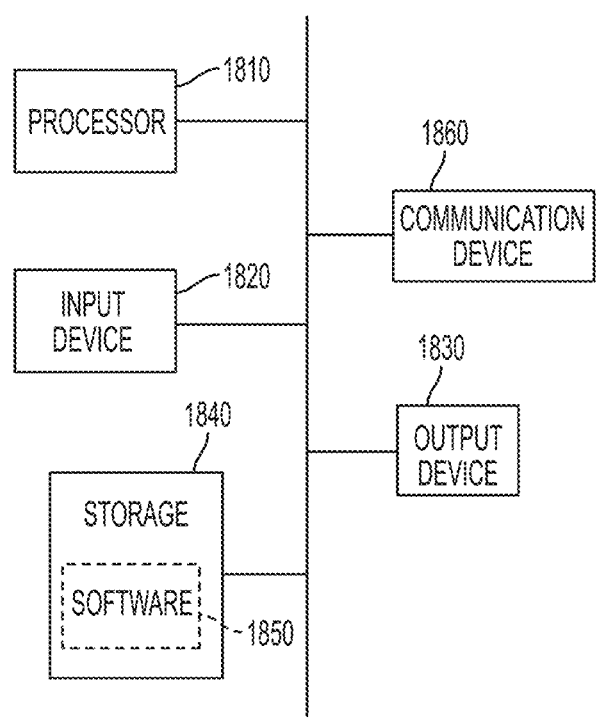
FIG. 18 illustrates an example computing device upon which examples of the disclosure can be implemented.

FIG. 18 illustrates an example of a computing device in accordance with one embodiment. Device 1800 can be a host computer connected to a network. Device 1800 can be a client computer or a server. As shown in FIG. 18, device 1800 can be any suitable type of microprocessor-based device, such as a personal computer, workstation, server or handheld computing device (portable electronic device) such as a phone or tablet. The device can include, for example, one or more of processor 1810, input device 1820, output device 1830, storage 1840, and communication device 1860. Input device 1820 and output device 1830 can generally correspond to those described above, and can either be connectable or integrated with the computer.

Input device 1820 can be any suitable device that provides input, such as a touch screen, keyboard or keypad, mouse, or voice-recognition device. Output device 1830 can be any suitable device that provides output, such as a touch screen, haptics device, or speaker.

Storage 1840 can be any suitable device that provides storage, such as an electrical, magnetic or optical memory including a RAM, cache, hard drive, or removable storage disk. Communication device 1860 can include any suitable device capable of transmitting and receiving signals over a network, such as a network interface chip or device. The components of the computer can be connected in any suitable manner, such as via a physical bus or wirelessly.

Software 1850, which can be stored in storage 1840 and executed by processor 1810, can include, for example, the programming that embodies the functionality of the present disclosure (e.g., as embodied in the devices as described above).

Software 1850 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1840, that can contain or store programming for use by or in connection with an instruction execution system, apparatus, or device.

Software 1850 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 1800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 1800 can implement any operating system suitable for operating on the network. Software 1850 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

The systems and methods described above can enable the implementation of a biomedical innovation datametrics dashboard. The systems and methods described above can be used to simulate the impact of governmental policy decisions on private research and development planning, and to perform multi-objective optimization utilizing such simulations, and thus to facilitate multiple-criteria decision-making in the biomedical innovation domain.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

What is claimed is:

1. An electronic simulation device for obtaining satisficing solutions to optimize public and private sector interactions using computational models, the device comprising:
   a processor, the processor configured to:
      receive data from one or more sources;
      perform one or more simulations based on the received data, wherein the one or more simulations are based on a plurality of models, one or more constraints provided by a user of the electronic device, and one or more objectives provided by the user of the device, wherein the simulations are configured to predict the outcomes of governmental policy scenarios, and wherein the plurality of models include at least one of: a policy and budget model, a private sector response model, an innovation development cycle model, or a population and disease model; and determine a satisficing strategy for the one or more objectives provided by the user, wherein determining a satisficing solution comprises:

defining a normalized objective function for each of the one or more objectives provided by the user of the device;

defining a preference function over a strategy space; and refining the strategy, wherein refining the strategy includes applying one or more perturbations to the one or more simulations.

2. The device of claim 1, wherein the data received from the one or more sources are used to initialize a base simulation population and disease attributes, and wherein the one or more simulations are based on the initialized base simulation population and disease attributes.

3. The device of claim 1, wherein receiving the data comprises:
downloading content from the one or more sources;
extracting the data from the downloaded content; and
transforming the extracted data into a common format.

4. The device of claim 1, wherein defining a normalized objective function comprises:
prompting the user for one or more minimum acceptability thresholds;
estimating one or more maximum feasibility values by performing a single-objective optimization on each objective of the one more objectives; and
defining the normalized objective function based on the one or more minimum acceptability thresholds and the one or more maximum feasibility values.

5. The device of claim 4, wherein defining a preference function comprises:
prompting the user for one or more strategy preferences; and
modifying the normalized objective function based on the user's one or more strategy preferences.

6. The device of claim 5, wherein the processor is further caused to select a satisficing strategy based on one or more user preferences, and wherein selecting a satisficing strategy includes searching for one or more preferred strategies by performing a single-objective optimization over a space of satisficing strategies using the defined preference function.

7. The device of claim 1, wherein refining the strategy includes prompting the user to indicate whether the one or more objectives should be improved, relaxed, or is acceptable and perturbing the strategy based on the user's indication.

8. A method for executing a computational simulation to obtain satisficing solutions to optimize public and private sector interactions, the method comprising:
receiving data from one or more sources;
performing one or more simulations based on the received data, wherein the one or more simulations are based on a plurality of models, one or more constraints provided by a user of the electronic device, and one or more objectives provided by the user of the device, wherein the simulations are configured to predict the outcomes of governmental policy scenarios, and wherein the plurality of models include at least one of: a policy and budget model, a private sector response model, an innovation development cycle model, or a population and disease model; and determining a satisficing strategy for the one or more objectives provided by the user, wherein determining a satisficing solution comprises:

defining a normalized objective function for each of the one or more objectives provided by the user of the device;

defining a preference function over a strategy space; and refining the strategy, wherein refining the strategy includes applying one or more perturbations to the one or more simulations.

9. The method of claim 8, wherein the data received from the one or more sources are used to initialize a base simulation population and disease attributes, and wherein the one or more simulations are based on the initialized base simulation population and disease attributes.

10. The method of claim 8, wherein receiving the data comprises:
downloading content from the one or more sources;
extracting the data from the downloaded content; and
transforming the extracted data into a common format.

11. The method of claim 8, wherein defining a normalized objective function comprises:
prompting the user for one or more minimum acceptability thresholds;
estimating one or more maximum feasibility values by performing a single-objective optimization on each objective of the one more objectives; and
defining the normalized objective function based on the one or more minimum acceptability thresholds and the one or more maximum feasibility values.

12. The method of claim 11, wherein defining a preference function comprises:
prompting the user for one or more strategy preferences; and
modifying the normalized objective function based on the user's one or more strategy preferences.

13. The method of claim 12, wherein the method further includes selecting a satisficing strategy based on one or more user preferences, and wherein selecting a satisficing strategy includes searching for one or more preferred strategies by performing a single-objective optimization over a space of satisficing strategies using the defined preference function.

14. The method of claim 8, wherein refining the strategy includes prompting the user to indicate whether the one or more objectives should be improved, relaxed, or is acceptable and perturbing the strategy based on the user's indication.

15. A non-transitory computer readable storage medium having stored thereon a set of instructions for executing a computational simulation to obtain satisficing solutions to optimize public and private sector interactions that when executed by a computing device, cause the computing device to:
receive data from one or more sources;
perform one or more simulations based on the received data, wherein the one or more simulations are based on a plurality of models, one or more constraints provided by a user of the electronic device, and one or more objectives provided by the user of the device, wherein the simulations are configured to predict the outcomes of governmental policy scenarios, and wherein the plurality of models include at least one of: a policy and budget model, a private sector response model, an innovation development cycle model, or a population and disease model; and determine a satisficing strategy for the one or more objectives provided by the user, wherein determining a satisficing solution comprises:

defining a normalized objective function for each of the one or more objectives provided by the user of the device;

defining a preference function over a strategy space; and refining the strategy, wherein refining the strategy includes applying one or more perturbations to the one or more simulations.

16. The non-transitory computer readable storage medium of claim 15, wherein the data received from the one or more sources are used to initialize a base simulation population and disease attributes, and wherein the one or more simulations are based on the initialized base simulation population and disease attributes.

17. The non-transitory computer readable storage medium of claim 15, wherein receiving the data comprises:
downloading content from the one or more sources;
extracting the data from the downloaded content; and
transforming the extracted data into a common format.

18. The non-transitory computer readable storage medium of claim 15, wherein defining a normalized objective function comprises:
prompting the user for one or more minimum acceptability thresholds;
estimating one or more maximum feasibility values by performing a single-objective optimization on each objective of the one more objectives; and
defining the normalized objective function based on the one or more minimum acceptability thresholds and the one or more maximum feasibility values.

19. The non-transitory computer readable storage medium of claim 18, wherein defining a preference function comprises:
prompting the user for one or more strategy preferences; and
modifying the normalized objective function based on the user's one or more strategy preferences.

20. The non-transitory computer readable storage medium of claim 19 wherein the device is further caused to, select a satisficing strategy based on one or more user preferences, and wherein selecting a satisficing strategy includes searching for one or more preferred strategies by performing a single-objective optimization over a space of satisficing strategies using the defined preference function.

21. The non-transitory computer readable storage medium of claim 15, wherein refining the strategy includes prompting the user to indicate whether the one or more objectives should be improved, relaxed, or is acceptable and perturbing the strategy based on the user's indication.

* * * * *